(12) United States Patent
Chen

(10) Patent No.: US 9,737,219 B2
(45) Date of Patent: Aug. 22, 2017

(54) METHOD AND ASSOCIATED CONTROLLER FOR LIFE SIGN MONITORING

(71) Applicant: MEDIATEK Inc., Hsin-Chu (TW)

(72) Inventor: Tung-Chien Chen, Taipei (TW)

(73) Assignee: MEDIATEK INC., Hsin-Chu (TW)

( * ) Notice: Subject to any disclaimer, the term of this patent is extended or adjusted under 35 U.S.C. 154(b) by 470 days.

(21) Appl. No.: 14/291,420

(22) Filed: May 30, 2014

(65) Prior Publication Data

US 2015/0342535 A1    Dec. 3, 2015

(51) Int. Cl.
| | |
|---|---|
| *A61B 5/024* | (2006.01) |
| *A61B 5/00* | (2006.01) |
| *A61B 5/08* | (2006.01) |
| *A61B 5/11* | (2006.01) |

(52) U.S. Cl.
CPC ............ *A61B 5/024* (2013.01); *A61B 5/0077* (2013.01); *A61B 5/0816* (2013.01); *A61B 5/1118* (2013.01)

(58) Field of Classification Search
CPC ..................................................... A61B 5/024
See application file for complete search history.

(56) References Cited

U.S. PATENT DOCUMENTS

| | | | |
|---|---|---|---|
| 4,350,164 A | 9/1982 | Allain, Jr. | |
| 7,212,128 B2 | 5/2007 | Schenker | |
| 8,189,043 B2 | 5/2012 | Schneider et al. | |
| 2009/0232395 A1* | 9/2009 | Sumiya .................. | H04N 5/208 382/167 |
| 2011/0251493 A1 | 10/2011 | Poh et al. | |
| 2012/0242501 A1* | 9/2012 | Tran ..................... | A61B 5/0024 340/870.02 |
| 2013/0035599 A1 | 2/2013 | De Bruijn et al. | |
| 2013/0077823 A1 | 3/2013 | Mestha et al. | |
| 2013/0245502 A1 | 9/2013 | Lange et al. | |

FOREIGN PATENT DOCUMENTS

EP     2517621 A1     10/2012

OTHER PUBLICATIONS

EzSleep; http://www.ezsleep.net/Frame/products_2_1.html (English translation with a brief explanation); Copyright © 2011 Platinum Team Co., Ltd.

(Continued)

*Primary Examiner* — Rochelle Turchen
(74) *Attorney, Agent, or Firm* — McClure, Qualey & Rodack, LLP

(57) ABSTRACT

A method for life sign monitoring and associated controller is provided. The method includes: obtaining a video signal, performing an activity modeling on the video signal to provide an activity signal, performing a vital sign extraction on the video signal to provide a vital sign, performing a filtering on the vital sign in view of the activity signal to suppress a correlation between the activity signal and the vital sign, and accordingly providing a filtered vital sign; and, according to the filtered vital sign and whether the activity signal exceeds an activity threshold range, providing a joint decision for categorizing result of life sign monitoring to one of a plurality of predetermined episodes.

9 Claims, 16 Drawing Sheets

(56) References Cited

OTHER PUBLICATIONS http://www.irhythmtech.com/; iRhythm—ZIO® Patch System; "ZIO® Service Proven to Capture Arrhythmias for Earlier Diagnosis";© 2014 iRhythm Technologies, Inc. All rights reserved.

Nuvant Mobile Cardiac Telemetrv; http://www.corventis.com/int/; May 29, 2014; pp. 1-3.

Wearable health monitoring; http://www2.imec.be/be_en/research/wearable-health-monitoring.html; May 29, 2014; pp. 1-2.

"Communication and Opto-Electronic (Information and Communication/Electronic and Opto-Electronic) Transferable Technology"; https://www.itri.org.tw/chi/techtransfer/04.asp?RootNodeId=040&NodeId=041&id=4190; (English translation with a brief explanation); Copyright © 2014; Industrial Technology Research Institute.

Poh, et al.: "Advancements in Noncontact, Multiparameter Physiological Measurements Using a Webcam"; IEEE Transactions on Biomedical Engineering, vol. 58, No. 1, Jan. 2011; pp. 7-11.

Fitbit® Official Site: Flex, One and Zip Wireless Activity and Sleep Trackers; http://www.fitbit.com/; © 2014 Fitbit Inc. All rights reserved.

UP24 by Jawbone; The UP System; https://jawbone.com/up; © 2014; pp. 1-11.

Owlet Baby Care; The Wireless iPhone Baby Breathing Monitor; http://www.owletcare.com/; © 2014 Owlet Baby Monitor; pp. 1-5.

UBabyCare; Smart Baby Mat, Intelligent Baby Movement Monitor; http://www.ubabycare.com/EN/index.html; Huijia Technology Co., Ltd.; Launch date Jul. 2011.

\* cited by examiner

METHOD AND ASSOCIATED CONTROLLER FOR LIFE SIGN MONITORING

FIELD OF THE INVENTION

The invention relates to life sign monitoring, and more particularly, to a method of extracting vital sign(s) and activity signal(s) from a video signal and associated apparatus, e.g., controller.

BACKGROUND OF THE INVENTION

Healthcare is essential in welfare of modern society, especially for infants, bedridden patients and elderly persons who need constant life sign monitoring. Such life sign monitoring is currently achieved by regular inspection of care-aid personnel, e.g., babysitters, nurses and/or medical doctors. However, monitoring relied on manual effort suffers from unintentional negligence and/or inexperience, causing interruption for those who need rest, and/or failure to immediately reflect medical emergency because of long inspection periods. Demands on automated and unattended life sign monitoring technology therefore emerge.

SUMMARY OF THE INVENTION

Though there are conventional hospital life sign monitoring instruments for institutionalized infants, patients and elderly persons, as well as portable life sign monitoring/detecting gadgets of various form factors, they rely on contact sensors attached to monitored subject, and/or invasive sensors intruded through skin of monitored subject. Uncomfortable attachment/invasion of sensor causes monitored subject to feel restricted and painful, even causes monitored subject to resist unconsciously or/and consciously, and consequently leads to incorrect sensing owing to loosed contact.

To address aforementioned issues, the invention provides automated, unattended, real-time and accurate life sign monitoring based on remote, non-contact, non-invasive, low-cost and easily deployed video capturing of monitored subject. From captured video signal, vital sign(s) and activity signal(s) are extracted. While video-extracted vital sign(s) may suffer artifact (noise) due to activity of monitored subject, video-extracted activity signal(s) indicative of activity of monitored subject will be leveraged to filter the vital sign(s), so the resultant filtered vital sign(s) can better quantify vital characteristics of the monitored subject. By collectively considering the vital sign(s) and the activity signal(s), the invention may provide a joint decision, which may categorize result of life sign monitoring to comprehensive episodes for convenient medial advice. For example, the episodes may include "so far so good" and "alarm," while the latter may trigger an alarm for immediate medical attention.

An objective of the invention is providing a method for life sign monitoring. The method may include: obtaining a video signal of a monitored subject; by a processor, performing an activity modeling on the video signal to provide a time-varying activity signal; performing a vital sign extraction on the video signal to provide a time varying vital sign; performing a filtering on the vital sign in view of the activity signal to suppress a correlation between the activity signal and the vital sign, and accordingly providing a filtered vital sign; and, according to the filtered vital sign (or the vital sign) and whether the activity signal exceeds a predetermined activity threshold range, providing a joint decision for categorizing result of life sign monitoring to one of a plurality of predetermined episodes.

Performing the vital sign extraction may include: identifying a region of interest (ROI) from each of a plurality of frames of the video signal, and performing a pixel operation on pixels of a number (one or more) of ROIs identified from same number of frames (e.g., one or more preceding frame(s) and/or current frame) to provide a current sample of the vital sign.

The pixel operation may be performed on the ROI of current frame, and include: calculating a statistic value (e.g., mean, maximum, minimum, or variation, etc.) over pixel data (e.g., intensity of a prime color channel, luma, chroma, etc.) of pixels of the ROI, and accordingly providing current sample of the vital sign. As an alternative example, the pixel operation may be performed on ROIs of current frame and a preceding frame, and include: estimating difference of the two ROIs, e.g., summing absolute differences between pixel data of the two ROIs, and accordingly providing current sample of the vital sign. The vital sign may be a signal having a waveform indicative of heartbeat pulses or respiration (breathing) movements of the monitored subject.

Performing the activity modeling may include: identifying an ROI from each of a plurality of preceding frames of the video signal; and performing an ROI operation on pixels of a number of ROIs identified from same number of frames (e.g., preceding frame(s) and/or current frame) to provide a current sample of the activity signal. Performing the ROI operation may include: performing a motion estimation between ROIs of different frames (e.g., preceding frame(s) and current frame), calculating area change between ROIs of different frames, summing absolute difference between pixel data of ROIs of different frames, and/or, calculating change of sum of pixel data between ROIs of different frames.

The activity signal may be a signal having a waveform indicative of small-scale movement (e.g., tremble, flutter, etc.) and/or large-scale motion (e.g., turning head, flipping body, changing posture, raising/lowering/moving hand/arm/leg, etc.) of the monitored subject.

Performing the filtering on the vital sign in view of the activity signal may include: buffering an amount of delayed samples by delaying the activity signal; respectively weighting the delayed samples by a same amount of weighting coefficients, and accordingly providing a weighted signal; subtracting the weighted signal from the vital sign to provide the filtered vital sign; and, adaptively and dynamically adjusting value of each weighting coefficient according to the filtered vital sign.

The vital sign or the filtered vital sign may include a plurality of channel signals, (e.g., red, blue and/or green channels), and the method may further include: performing an independent component analysis (ICA) on the channel signals, and accordingly providing a plurality of component signals; performing spectrum analysis on the component signal(s) to obtain spectrum(s), and identifying a characteristic value of the spectrum(s) (e.g., a frequency with a magnitude which maximizes over all the spectrum(s)), so as to provide a current sample of the derived vital sign. For example, the derived vital sign may be a signal indicative of heartbeat rate (counts of heartbeats per unit time), or respiration rate.

The method may further include: providing a first derived vital sign and performing a signal pre-processing on the first derived vital sign; performing an ICA on the pre-processed first derived vital sign and the vital sign (or the filtered vital sign) to provide a plurality of component signals; and, according to the component signals, providing a second derived vital sign.

The joint decision may be provided by checking if the activity signal exceeds the activity threshold range and if the derived vital sign exceeds a vital threshold range; if both are false, the joint decision may reflect an alarm episode, since activity and vital reading are both low; on the contrary, if either one is true, the joint decision may reflect an episode of "so far so good."

The invention further provides a controller for life sign monitoring; the controller may include an interface, an activity modeling block, a vital sign extraction block, a filter block, a vital sign derivation block and a joint decision maker. The interface is capable of obtaining a video signal V0.

The activity modeling block performs an activity modeling on the video signal V0 to provide a number P (one or more) of activity signals a[t]_1 to a[t]_P. The activity modeling block may process the video signal V0 (e.g., perform background subtraction on the video signal) to obtain a video signal V1, which includes sequential frames V1[.], e.g., V1[t-2*dt], V1[t-dt] and V1[t], etc. Then the activity modeling block may perform subject recognition on the video signal V1 to identify the monitored subject; and, according to the identified subject, further identify a number M1 (one or more) of ROIs aR[t]_1 to aR[t]_M1 from each frame V1[t]; for example, each ROI aR[t]_m (m=1 to M1) may track a body part of the identified subject, e.g., face, chest, arm, hand and/or combination of the parts, etc. ROIs tracking the same body part on different frames, e.g., ROIs aR[t-2*dt]_m, aR[t-dt]_m and aR[t]_m identified from frames V1[t-2*dt], V1[t-dt] and V1[t], collectively form an ROI sequence denoted as aR[.]_m.

On a number of sequential (preceding and/or current) ROIs aR[.]_m respectively tracking the same body part from same number of sequential frames V1[.], the activity modeling block may further perform an ROI operation, and accordingly provide a current sample of an activity signals a[t]_p (one of the activity signals a[t]_1 to a[t]_P). For example, the activity modeling block may perform the ROI operation on a number (J1+1) of sequential ROIs aR[t-J1*dt]_m, aR[t-(J1-1)*dt]_m, . . . , aR[t-2*dt]_m, aR[t-dt]_m and aR[t]_m respectively extracted from the frames V1[t-J1*dt] to V1[t], and accordingly provide a current sample of the activity signal a[t]_p.

The activity modeling block may perform the ROI operation by: performing a motion estimation between ROIs of different frames; calculating area change between ROIs of different frames; summing absolute difference between ROIs of different frames; and/or, calculating change of sum of intensity between ROIs of different frames.

The vital sign extraction block performs a vital sign extraction on the video signal to provide a number Q (one or more) vital signs signal v[t]_1 to v[t]_Q. The vital sign extraction block may perform the vital sign extraction by: identifying a number M2 of ROIs vR[t]_1 to vR[t]_M2 from each frame V0[t] of the video signal V0 to respectively form ROI sequences vR[.]_1 to vR[.]_M2. On pixels of a number of ROIs of an ROI sequence vR[.]_m' (one of the ROI sequences vR[.]_1 to vR[.]_M2), e.g., on pixels of the ROI(s) vR[t-dt]_m' and/or vR[t]_m' identified from preceding and/or current frame(s) V0[t-dt] and/or V0[t], the vital sign extraction block is further capable of performing a pixel operation, and accordingly provide a sample of a vital sign v[t]_q (one of the vital signs v[t]_1 to v[t]_Q).

The filter block may include a number K (one or more) of filter U_1 to U_K, each filter U_k (k=1 to K) is capable of performing a filtering on an input signal x[t]_k (e.g., one of the vital signs v[t]_to v[t]_Q) in view of a reference signal z[t]_k (e.g., one of the activity signals a[t]_1 to a[t]_P) to suppress a correlation between the reference signal z[t]_k and the input signal x[t]_k, and accordingly providing a filtered vital sign fv[t]_k. Collectively, the number K of filters U_1 to U_K provide same number K of filtered vital sign fv[t]_1 to fv[t]_K.

The joint decision maker provides a joint decision for categorizing result of life sign monitoring to one of a plurality of predetermined episodes, according to a subset (one, some or all) of the activity signals a[t]_1 to a[t]_K and a subset (one, some or all) of the vital signs v[t]_1 to v[t]_Q, fv[t]_1 to fv[t]_K and rv[t]_1 to rv[t]_N.

Numerous objects, features and advantages of the invention will be readily apparent upon a reading of the following detailed description of embodiments of the invention when taken in conjunction with the accompanying drawings. However, the drawings employed herein are for the purpose of descriptions and should not be regarded as limiting.

BRIEF DESCRIPTION OF THE DRAWINGS

The above objects and advantages of the invention will become more readily apparent to those ordinarily skilled in the art after reviewing the following detailed description and accompanying drawings, in which.

DETAILED DESCRIPTION OF PREFERRED EMBODIMENTS

Figure 1:
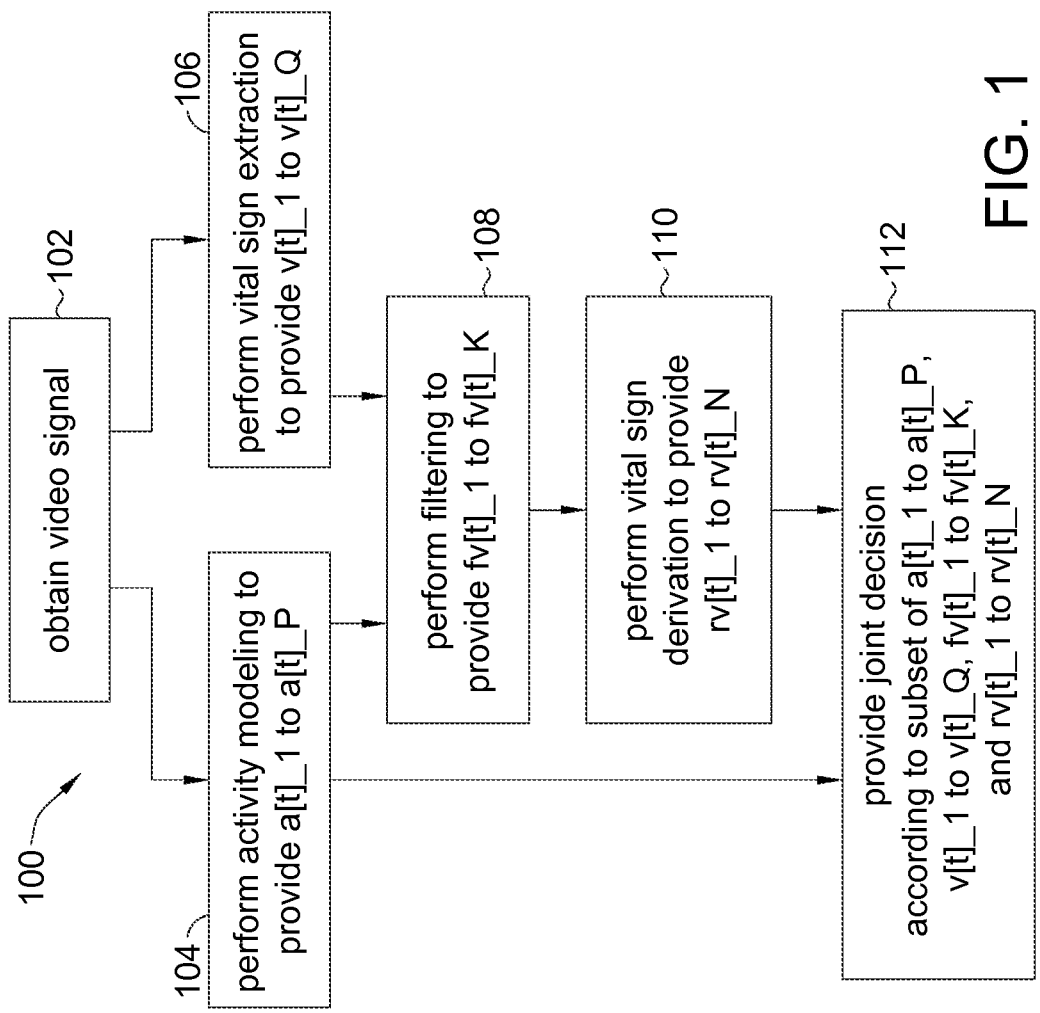
FIG. 1 illustrates a procedure according to an embodiment of the invention.
Figure 2:
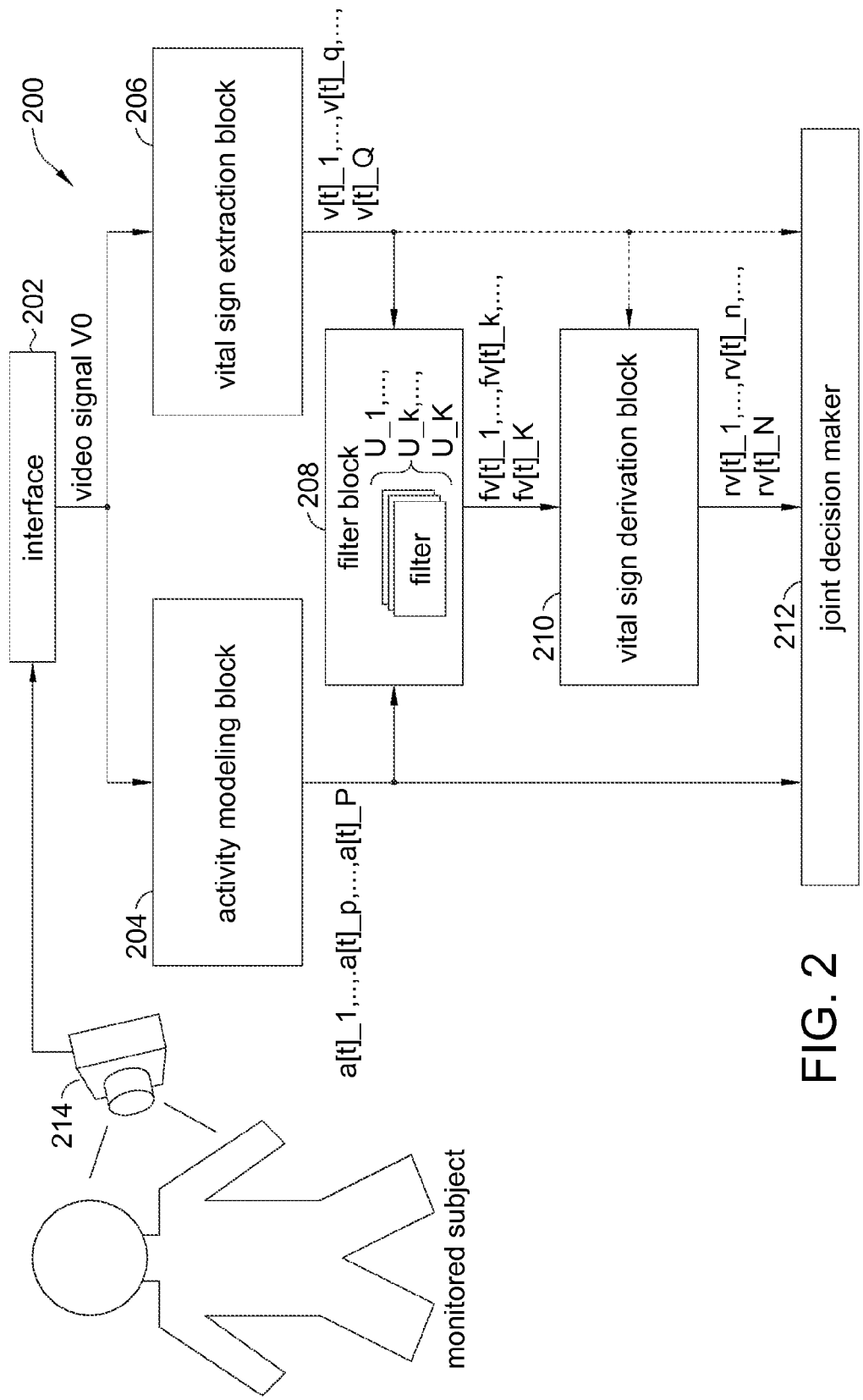
FIG. 2 illustrates a controller (or processor) according to an embodiment of the invention.

Please refer to FIG. 1 and FIG. 2. FIG. 1 illustrates a procedure 100 for life sign monitoring according to an embodiment of the invention. FIG. 2 illustrates a controller (or processor) 200 according to an embodiment of the invention. The processor 200 may execute the procedure 100 to implement automatic life sign monitoring. For example, the processor 200 may be an integrated circuit or an electronic system including multiple integrated systems, and is capable of executing the procedure 100 in FIG. 1.

As shown in FIG. 2, the processor 200 may include an interface 202, an activity modeling block 204, a vital sign extraction block 206, a filter block 208, a vital sign derivation block 210 and a joint decision maker 212. Each of the blocks 204, 206, 208 and 210, as well as the joint decision maker 212, may be implemented by dedicated circuitry, and/or be implemented by a general processing hardware (not shown) which executed associated software and/or firmware code(s).

In the processor 200, the interface 202 is capable of obtaining a video signal V0 which contains images (frames) of a monitored subject. For example, the interface 202 may include mechanical connector (e.g., USB connector or HDMI connector, not shown) to physically connect a video camera 214 (or multiple video cameras) by wire/cable, and receive video stream captured by the video camera 214 to accordingly obtain the video signal V0. The interface 202 may include network circuitry for accessing wired and/or wireless network(s) to obtain the video signal V0 provided by a remote video camera 214 and/or a storage device (not shown), e.g. hard disk drive(s), flash memory, and/or volatile memory, etc. The interface 202 may also include conversion circuitry (not shown), such as analog to digital converter(s), for converting raw video stream of video camera to the video signal V0. The video signal V0 may include a plurality of frames, e.g., frames $V0[t-2*dt]$, $V0[t-dt]$ and $V0[t]$ respectively at times (t-2*dt), (t-dt) and t.

The activity modeling block 204 is capable of performing an activity modeling on the video signal V0 to provide a number P (one or more) of activity signals $a[t]\_1$ to $a[t]\_P$. Each activity signal $a[t]\_p$ (p=1 to P) may be a signal having a waveform indicative of small-scale movement (e.g., tremble, flutter, etc.) and/or large-scale motion (e.g., turning head, flipping body, changing posture, raising/lowering/moving hand/arm/leg, etc.) of the monitored subject.

The vital sign extraction block 206 performs a vital sign extraction on the video signal V0 to provide a number Q (one or more) of vital signs $v[t]\_1$ to $v[t]\_Q$. Each vital sign $v[t]\_q$ (q=1 to Q) may be a signal having a waveform indicative of heartbeat pulses, respiration movements, temporal rhythm of blood pressure or temporal fluctuation of blood oxygen saturation, etc., of the monitored subject.

One, some or all of the vital signs $v[t]\_1$ to $v[t]\_Q$ may suffer from artifact, interference and/or noise caused by activity of the monitored subject. To suppress the artifact, interference and/or noise, the filter block 208 may include a number K (one or more) of filters $U\_1$ to $U\_K$, each filter $U\_k$ (k=1 to K) filters on an input signal (e.g., one of the vital signs $v[t]\_1$ to $v[t]\_Q$) in view of a reference signal (e.g., one of the activity signals $a[t]\_1$ to $a[t]\_P$) to suppress a correlation between the reference signal and the input signal, and accordingly providing a filtered vital sign $fv[t]\_k$. That is, by leveraging the activity signal $a[t]\_p$ reflecting activity of the monitoring subject, activity induced artifact, interference and/or noise within the vital sign $v[t]\_q$ may be filtrated, so as to provide the filtered vital sign $fv[t]\_k$ of better signal quality. Alternatively, the filters $U\_1$ to $U\_K$ may provide same number K of filtered vital signs $fv[t]\_1$ to $fv[t]\_K$.

The vital sign derivation block 210 may perform vital sign derivation on one or more of the vital signs $v[t]\_1$ to $v[t]\_Q$ and the filtered vital signs $fv[t]\_1$ to $fv[t]\_K$, and accordingly provide a number N (one or more) of derived vital signs $rv[t]\_1$ to $rv[t]\_N$. For example, a derived vital sign $rv[t]\_n$ (one of the derived vital signs $rv[t]\_1$ to $rv[t]\_N$) may be a signal indicative of heartbeat rate (counts of heartbeats per unit time), or respiration rat, etc.

The joint decision maker 212 performs a joint decision for categorizing result of life sign monitoring to one of a plurality of predetermined episodes, collectively according to a subset (e.g., one, some or all) of the vital signs $v[t]\_1$ to $v[t]\_Q$, $fv[t]\_1$ to $fv[t]\_K$ and $rv[t]\_1$ to $rv[t]\_N$, as well as a subset of the activity signals $a[t]\_1$ to $a[t]\_K$. For example, the joint decision maker 212 may utilize one of the activity signals $a[t]\_1$ to $a[t]\_K$ as an activity indicator, along with one of the vital signs $v[t]\_1$ to $v[t]\_Q$, $fv[t]\_$ to $fv[t]\_K$ and $rv[t]\_1$ to $rv[t]\_N$ as a vital indicator. Jointly considering the activity indicator and the vital indicator, the joint decision maker 212 may provide joint decision by checking if the activity indicator exceeds an associated activity threshold range (e.g., is less than a lower bound of the activity threshold range) and if the vital indicator exceeds an associated vital threshold range (e.g., is less than a lower bound of the vital threshold range). If both are false, the joint decision may reflect an alarm episode, since activity and vital reading are both low. On the contrary, if either one is true, the joint decision may reflect an episode of "so far so good."

Along with the processor 200 shown in FIG. 2, major steps of the procedure 100 shown in FIG. 1 may be described as follows.

Step 102: by the interface 202 (FIG. 2), obtain the video signal V0.

Step 104: by the activity modeling block 204, perform activity modeling on the video signal V0 to provide the time-varying activity signals $a[t]\_1$ to $a[t]\_P$.

Step 106: by the vital sign extraction block 206, perform vital sign extraction on the video signal V0 to provide the time varying preliminary vital signs $v[t]\_1$ to $v[t]\_Q$.

Step 108: by each filter unit $U\_k$ of the filter block 208, perform filtering on one of the vital signs $v[t]\_1$ to $v[t]\_Q$ and $rv[t]\_1$ to $rv[t]\_N$ in view of one of the activity signals $a[t]\_1$ to $a[t]\_P$, so as to suppress a correlation between them, and accordingly provide a filtered vital sign $fv[t]\_k$ as one of the filtered vital signs $fv[t]\_1$ to $fv[t]\_K$. Collectively with the filters $U\_1$ to $U\_K$, the filtered vital signs $fv[t]\_1$ to $fv[t]\_K$ are provided.

Step 110: by the vital sign derivation block 210, perform vital sign derivation on a subset (one, some or all) of the vital signs $v[t]\_1$ to $v[t]\_Q$ and $fv[t]\_1$ to $fv[t]\_K$, and accordingly provide the derived vital signs $rv[t]\_1$ to $rv[t]\_N$.

Step 112: by the joint decision maker 212, provide a joint decision for categorizing result of life sign monitoring to one of a plurality of predetermined episodes, according to a subset (one, some or all) of the vital signs $v[t]\_1$ to $v[t]\_Q$, $fv[t]\_1$ to $fv[t]\_K$ and $rv[t]\_1$ to $rv[t]\_N$, as well as a subset (one, some or all) of the activity signals $a[t]\_1$ to $a[t]\_K$.

In the procedure 100, steps 104 and 106 may be executed concurrently or sequentially, steps 104 and 108 may be executed concurrently or sequentially, and steps 104 and 110 may be executed concurrently or sequentially. Every two of the numbers P, Q, K and R may be identical or different. For example, the number Q may be different from the number P but equal to the number K.

Figure 3:
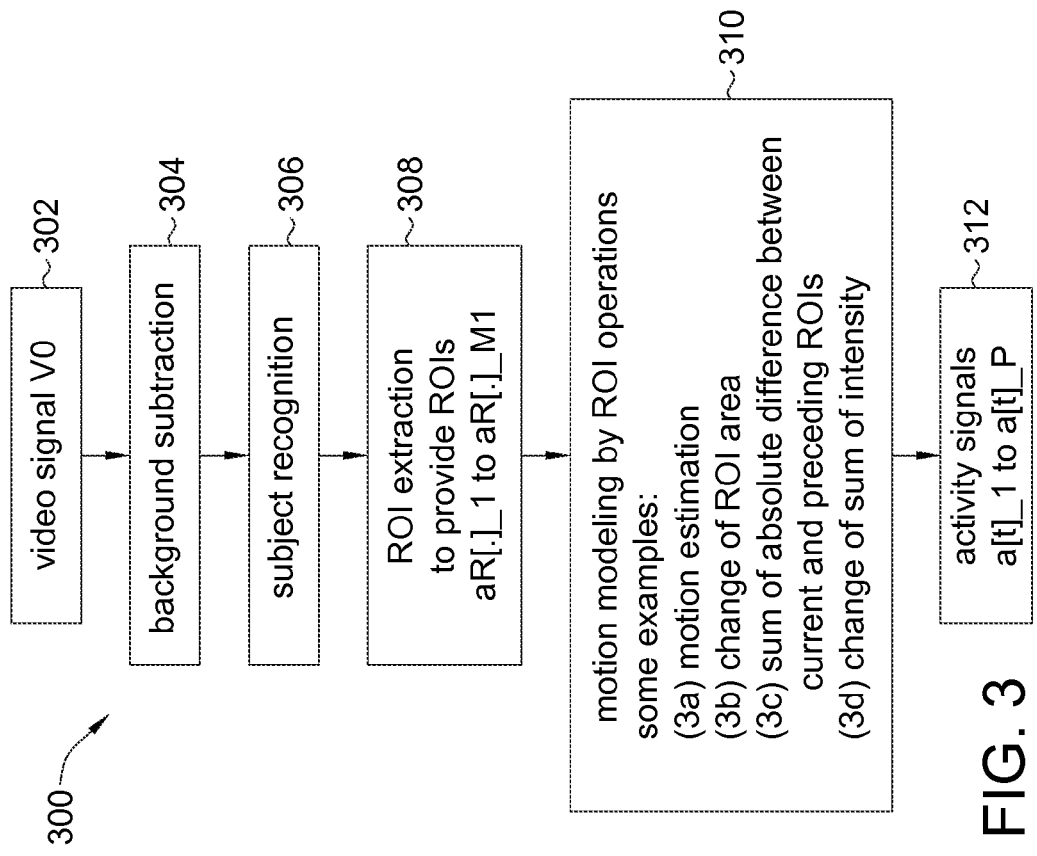
FIG. 3 illustrates a procedure, according to an embodiment of the invention, for activity modeling shown in FIG. 1.

Along with FIG. 1 and FIG. 2, please refer to FIG. 3 illustrating a procedure 300 according to an embodiment of the invention. The activity modeling block 204 (FIG. 2) may execute the procedure 300 to implement step 104 (FIG. 1). The procedure 300 may include the following steps.

Step 302: receive a video signal V0.

Step 304: perform background subtraction, e.g., by: for a current frame V0[$t$] and a preceding frame V0[$t$-dt] of the video V0, identifying still background according to a common portion of the frames V0[$t$-dt] and V0[$t$], subtracting the background from the frame V0[$t$], and accordingly providing a current background-subtracted frame V1 [t] (not shown). Alternatively, the background subtraction may be performed by: for a current frame V0[$t$] and a plurality of preceding frames V0[$t$-dt], V0[$t$-2*dt] to V0[$t$-J0*dt], identifying background according to the frame V0[$t$] and an average (or weighted average) of the frames V0[$t$-dt] to V0[$t$-J0*dt], and accordingly providing the frame V1[$t$]. Then, a background-subtracted video signal V1 (not shown) is obtained from background-subtracted frames, e.g., frame V1 [t-dt] for time (t-dt) and frame V1 [t] for time t, etc.

Step 306: by the activity modeling block 204, perform subject recognition on the video signal V1 by recognizing and identifying the monitored subject from each frame of the video signal V1. The subject recognition may base on face recognition, and/or base on comparing content of the video signal V1 with known patterns of the monitored subject.

Step 308: by the activity modeling block 204, perform ROI extraction on the recognized subject of each frame V1[$t$] by identifying a number (one or more) of body parts (e.g., face, chest, arm, hand and/or their combination, etc.) as a number M1 of ROIs aR[t]_1 to aR[t]_M1 (not shown). Hence, from sequential frames V1[.], the activity modeling block 204 may respectively extract number M1 of ROI sequences respectively denoted as aR[.]_1 to aR[.]_M1, with each ROI sequence aR[.]_m (m=1 to M1) tracking a same body part from sequential frames V1[.]. For example, the ROI sequence aR[.]_m may include ROIs aR[t-2*dt]_m, aR[t-dt]_m, aR[t]_m, . . . to track the same body part respectively identified and extracted from the frames V1[$t$-2*dt], V1[$t$-dt], V1[$t$], . . . etc.

Step 310: to provide each activity signal a[t]_p (p=1 to P), perform an ROI operation on an associated ROI sequence aR[.]_m (one of the ROI sequences aR[.]_1 to aR[.]_M1), by the activity modeling block 204. For example, the activity modeling block 204 may perform the ROI operation on a number (J1+1) of sequential ROIs aR[t-J1*dt]_m, aR[t-(J1-1)*dt]_m, . . . , aR[t-2*dt]_m and aR[t]_m respectively extracted from the frames V1[$t$-J1*dt] to V1[$t$], and accordingly provide a current sample (at time t) of the activity signal a[t]_p.

There are various ROI operation algorithms for implementation for providing each activity signal a[t]p, such as the algorithms (3$a$) to (3$d$) shown in FIG. 3. To provide the activity signal a[t]_p by the algorithm (3$a$), the activity modeling block 204 may implement the ROI operation by performing a motion estimation between a current ROI aR[t]_m and a preceding ROI aR[t-dt]_m of the same ROI sequence aR[.]_m, and accordingly provide a motion vector MV[t] (not shown) for current time t. Hence, vector length (norm) of the motion vector MV[t], or angle of the motion vector MV[t], or collectively both length and angle of the motion vector MV[t], may be provided as a current sample of the activity signal a[t]_p. Alternatively, x component or y component of the motion vector MV[t], or collectively both x component and y component, may be provided as the activity signal a[t]_p.

According to the algorithm (3$b$), the activity modeling block 204 may perform the ROI operation by calculating area change between area of a current ROI aR[t]_m and area of a preceding ROI aR[t-dt]_m, and hence provide a current sample of the activity signal a[t]_p. For example, assuming the area of the ROI aR[t]_m occupies a count PXC[t] of pixels, and the area of the ROI aR[t-dt]_m occupies a count PXC[t-dt] of pixels, then their difference (PXC[t]-PXC[t-dt]) may be provided as a current sample of the activity signal a[t]_p. Alternatively, the activity modeling block 204 may calculate difference between the area of the current ROI aR[t]_m and an average (or weighted average) area of a plurality of preceding ROIs aR[t-dt]_m to aR[t-J21]_m, and accordingly provide a current sample of the activity signal a[t]_p. Alternatively, the activity modeling block 204 may calculate a linear combination of the areas of the ROIs aR[t]_m to aR[t-J2*t]_m, and accordingly provide a current sample of the activity signal a[t]_p.

According to the algorithm (3$c$), the activity modeling block 204 may perform the ROI operation by summing absolute difference between the ROIs aR[t]_m and aR[t-dt]_m from the frames V1[$t$] and V1[$t$-dt], so as to provide a current sample of the activity signal a[t]p.

According to the algorithm (3$d$), the activity modeling block 204 may perform the ROI operation by calculating change of sum of intensity of two (or more) ROIs aR[t]_m and aR[t-dt]_m, and accordingly provide the activity signal a[t]_p. For example, for a current time t, the activity modeling block 204 may sum intensity of all pixels within the preceding ROI aR[t-dt]_m, and obtain a sum SM[t-dt]. Also, the activity modeling block 204 may sum intensity of all pixels within the current ROI aR[t]_m, and obtain another sum SM[t]. Then, the activity modeling block 204 may calculate change between the sums SM[t] and SM[t-dt], and accordingly obtain a current sample of the activity signal a[t]_p. Alternatively, the activity modeling block 204 may calculate a linear combination (weighted sum) of the intensity sums SM[t], SM[t-dt] to SM[t-J3*dt] of the frames V1[$t$], V1[$t$-dt] to V1[$t$-J3*dt] as a current sample of the activity signal a[t]_p. Intensity of a pixel may be luma, brightness, or a linear combination of red, green and blue color channel data of the pixel.

During step 310, while providing different two activity signals a[t]_p1 and a[t]_p2 of the activity signals a[t]_1 to a[t]_P, the activity modeling block 204 may perform two ROI operations of different ROI operation algorithms (e.g., different two of the algorithms (3$a$) to (3$d$)) on the same ROI sequence aR[.]_m, or respectively on different ROI sequences aR[.]_m1 and aR[.]_m2 (different two of the ROI sequences aR[.]_1 to aR[.]_M1). To provide different activity signals a[t]_p3 and a[t]_p4, the activity modeling block 204 may perform ROI operations of the same ROI operation algorithm respectively on different ROI sequences aR[.]_m3 and aR[.]_m4.

Step 312: Obtain the resultant activity signals a[t]_1 to a[t]_P.

Figure 4:
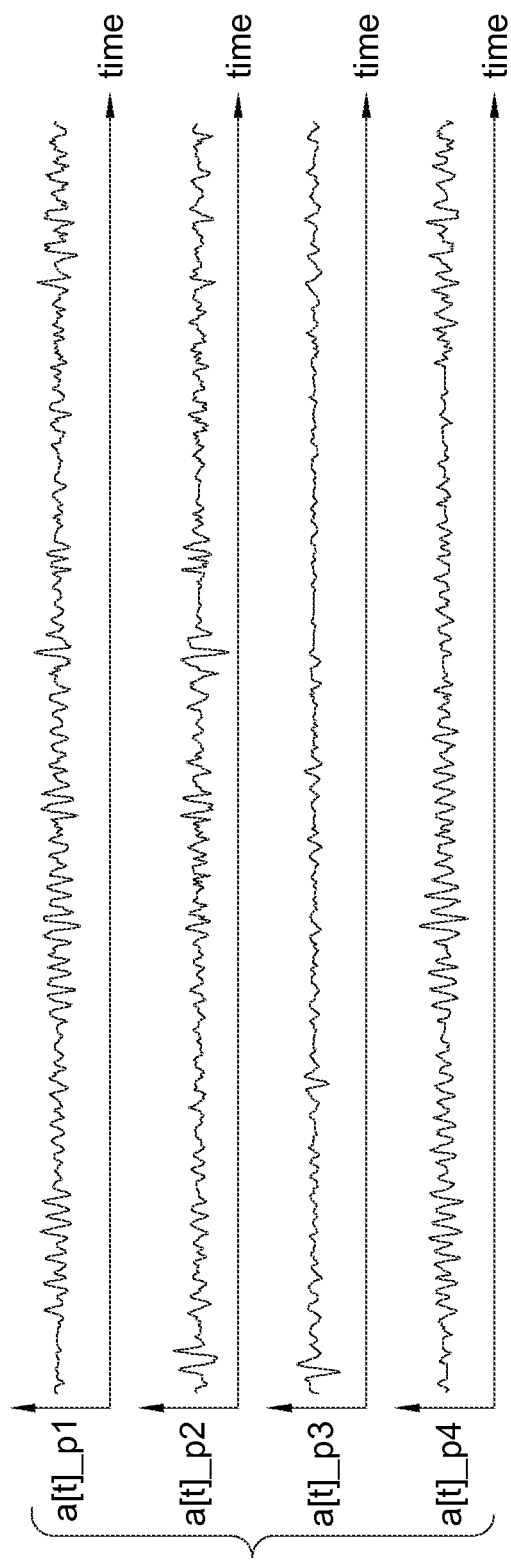
FIG. 4 demonstrates illustrative waveform examples of activity signals shown in FIG. 3.

For step 310, performing different ROI operations of different ROI operation algorithms on a same ROI sequence aR[.]_m may respectively reflect different aspects of the activity of the ROI sequence aR[.]_m. For example, assuming the ROI sequence aR[.]_m is associated to face of the monitored subject, the algorithm (3$a$) may be suitable to reflect translation (shift) movement of the face, and the algorithm (3$b$) may be suitable to reflect rotation of the face (e.g., shaking head). If the monitored subject is shaking head, an activity signal a[t]_p1 obtained by algorithm (3$a$) may be low but another activity signal a[t]_p2 obtained by algorithm (3$b$) may be high; on the other hand, if the monitored subject is nodding head with face remained forward, the activity signal a[t]_p1 may be high but the activity signal a[t]_p2 may be low. Accordingly, activity signals obtained by applying different ROI operation algorithms to different body parts (different ROI sequences) may collectively provide complete and thorough observation on activity of the monitored subject. FIG. 4 illustrates waveform examples of four activity signals a[t]_p1, a[t]_p2, a[t]_p3 and a[t]p4 respectively obtained by applying the algorithms (3a) to (3d) of FIG. 3 to an ROI of face.

Figure 5:
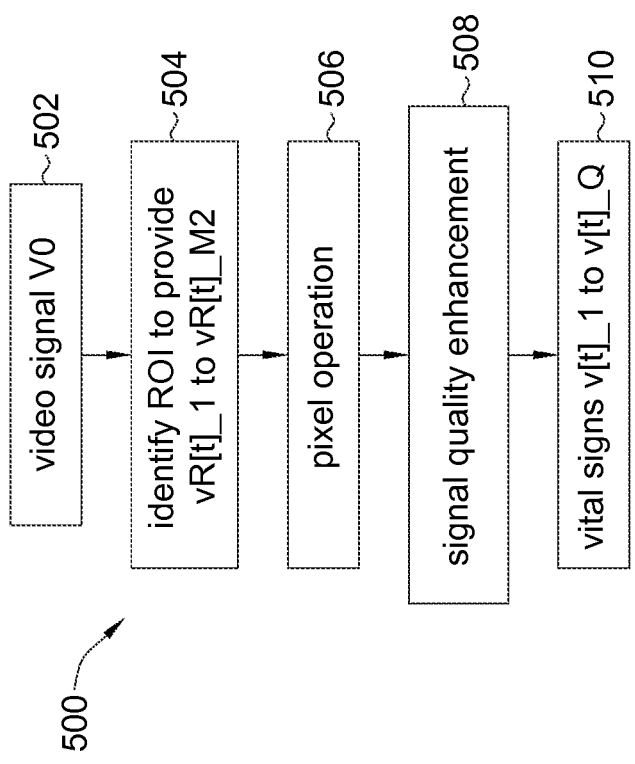
FIG. 5 illustrates a procedure, according to an embodiment of the invention, for vital sign extraction shown in FIG. 1.

Along with FIG. 1 and FIG. 2, please refer to FIG. 5 for a procedure 500 according to an embodiment of the invention. During step 106 (FIG. 1), the vital sign extraction block 206 (FIG. 2) may execute the procedure 500 to provide the vital signs v[t]_1 to v[t]_Q. For example, a vital sign v[t]_q (one of the vital signs v[t]_1 to v[t]_Q) may be a signal having a waveform indicative of heartbeat pulses or respiration motion of the monitored subject.

Step 502: start the procedure 500 with the video signal V0. The vital sign extraction block 206 may proceed to other steps of the procedure 500 with the original video signal V0; alternatively, the vital sign extraction block 206 may perform preliminary image processing on the video signal V0, e.g., noise-filtering, edge enhancing, de-blurring, de-blocking, white balancing, brightness adjusting, contrast adjusting, gamma tuning, and/or other color-tuning, and then proceed to other steps of the procedure 500 with the processed video signal V0.

Step 504: by the vital sign extraction block 206, identify a number M2 (one or more) of ROIs vR[t]_1 to vR[t]_M2 from each frame V0[$t$] of the video signal V0. For example, an ROI vR[t]_m' (one of the ROIs vR[t]_1 to vR[t]_M2) may be a region indicating a body part (e.g., face) or a union of several body parts (e.g., face, neck and chest) of the monitored subject. To identify the ROI vR[t]_m' from the frame V0[$t$], the vital sign extraction block 206 may perform pattern recognition (e.g., face detection) and tracking, so as to preliminarily locate the body part. For example, the vital sign extraction block 206 may identify, on the frame V0[$t$], a rectangular region which confines the body part(s) to be tracked. Then, the vital sign extraction block 206 may further apply skin-color segmentation on pixels of the rectangular region. If a pixel in the rectangular region has a color which falls in a predefined color range indicative of skin color; then the pixel is included in the ROI vR[t]_m'. That is, in the rectangular region, pixels with colors met the predefined color range collectively form the ROI vR[t]_m'.

Figure 6:
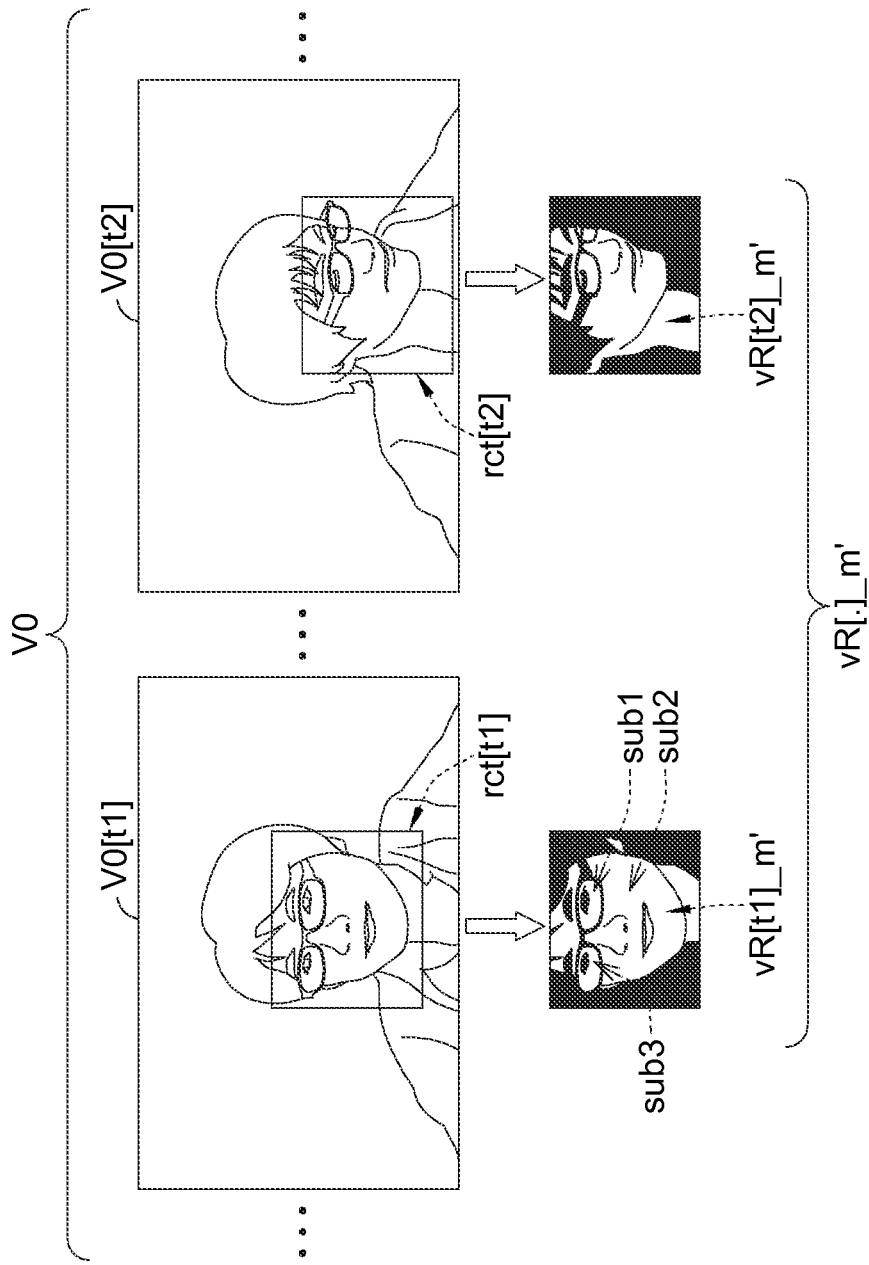
FIG. 6 to FIG. 8 demonstrate illustrative operation examples during the procedure in FIG. 5.

From sequential frames V0[.], the vital sign extraction block 206 may provide an ROI sequence vR[.]_m' tracking the same body part(s). For example, the ROI sequence vR[.]_m' may include ROIs vR[t-2*dt]_m', vR[t-dt]_m' and vR[t]_m' to track the same body part(s) respectively identified from the frames V0[$t$-2*dt], V0[$t$-dt] and V0[$t$]. As an illustrative example, FIG. 6 demonstrates two ROIs vR[t1]_m' and vR[t2]_m' of the same ROI sequence vR[.]_m' which tracks face (and neck, chest) of monitored subject (a person wearing glasses, for example). The two ROIs vR[t1]_m' and vR[t2]_m' are respectively identified from two frames V0[$t$1] and V0[$t$2] by applying step 504 (FIG. 5) to the video signal V0. At step 504, two rectangular regions rct[t1] and rct[t2] may first be identified from the two frames V0[$t$1] and V0[$t$2] by face detection and tracking; then, skin color segmentation is applied to pixels within the regions rct[t1] and rct[t2]. In the region rct[t1], pixels with colors met a skin color range are included in the ROI vR[t1]_m', while pixels with color not met the skin color range (i.e., pixels in shaded region of FIG. 6) are excluded. Similarly, in the region rct[t2], pixels with colors met the skin color range are included in the ROI vR[t2]_m'. As shown in FIG. 6, an ROI (e.g., vR[t1]_m' or vR[t2]_m') may be irregularly shaped, and may include mutually disconnected sub-regions. For example, the ROI vR[t1]_m' includes isolated sub-regions sub1, sub2 and sub3.

Step 506 (FIG. 5): to provide each vital sign v[t]_q (q=1 to Q), perform a pixel operation on an associated ROI sequence vR[.]_m' (one of the sequences vR[.]_1 to vR[.]_M2), by the vital sign extraction block 206. There may be various pixel operation algorithms to implement the pixel operation.

In a first pixel operation algorithm, the pixel operation may be performed on the single ROI vR[t]_m' of the current frame V0[$t$], and include: calculating a first statistic value, a second statistic value and a third statistic value (e.g., mean, maximum, minimum, variation, etc.) over a red channel pixel data, a green channel pixel data and a blue channel pixel data of pixels of the ROI vR[t]_m' to provide samples of a first channel signal ch1[$t$]_q, a second channel signal ch2[$t$]_q and a third channel signal ch3[$t$]_q, respectively. Then the channel signals ch1[$t$]_q, ch2[$t$]_q and ch3[$t$]_q may be collectively regarded as the vital sign v[t]_q. Alternatively, the channel signals ch1[$t$]_q to ch3[$t$]_q may be respectively obtained by calculating statistic values over luma, hue, and saturation of pixels of the ROI vR[t]_m'. In general, the vital sign v[t]_q may include one or more channel signals chx[t]_q, each channel signal chx[t]_q may be obtained by calculating a statistic value over indication data of pixels of the ROI vR[t]_m', and the indication data of a pixel is an associated linear combination of red, green and blue color channel data of the pixel.

Figure 7:
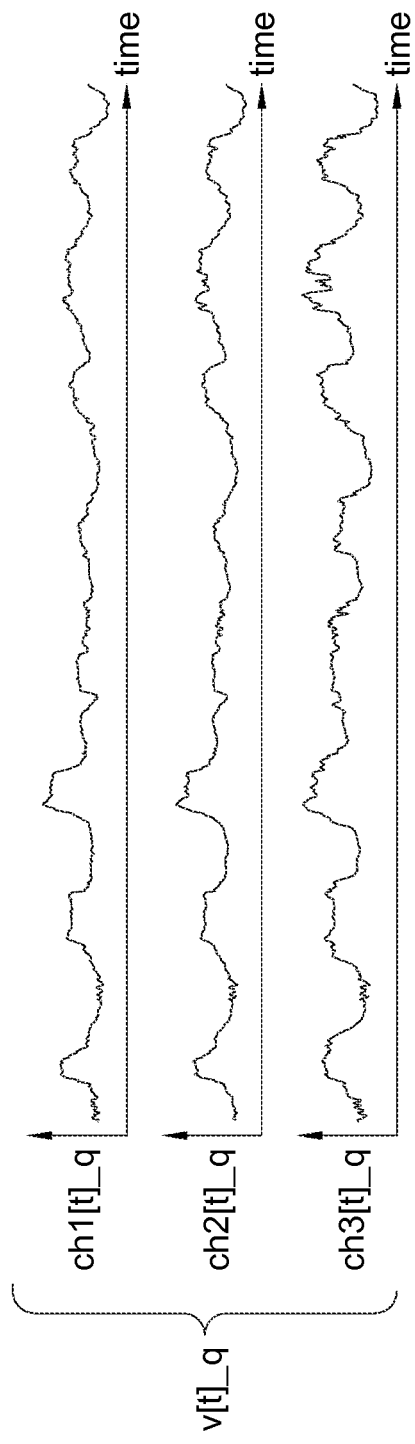

By applying the first pixel algorithm to a face-tracking ROI sequence vR[.]_m' (e.g., the ROI sequence shown in FIG. 6), the resultant vital sign v[t]_q may be adopted to indicate waveform of heartbeat pulses. For example, FIG. 7 illustrates exemplary waveforms of the red, green and blue channel signals ch1[$t$]_q to ch3[$t$]_q collectively included in a vital sign v[t]_q, a current sample of the red (green, blue) channel signal ch1[$t$]_q (ch2[$t$]_q, ch3[$t$]_q) may be obtained by averaging red (green, blue) channel data over pixels of a current ROI vR[t]_m'. Each of the channel signals ch1[$t$]_q to ch3[$t$]_q may also be individually regarded as a vital sign.

In a second pixel operation algorithm, the pixel operation in step 506 may be performed on several (preceding and/or current) ROIs of the ROI sequence vR[t]_m' to obtain the resultant vital sign v[t]_q, and include: calculating a statistic value (e.g., mean, sum of absolute difference, etc.) over pixel data (e.g., color channel data, luma, etc.) of different ROIs identified from different frames (e.g., ROIs vR[t-dt]_m' and vR[t]_m' of the frames V0[$t$-dt] and V0[$t$]), and accordingly providing a current sample of the vital sign v[t]_q. By applying the second pixel algorithm to an ROI sequence vR[.]_m' which tracks chest or a union of chest and face, the resultant vital sign v[t]_q may be adopted to indicate waveform of respiration movement. Similar to the first pixel operation algorithm, the vital sign v[t]_q obtained according to the second pixel operation algorithm may include several channel signals.

In step 506 (FIG. 5), the vital sign extraction block 206 may perform two pixel operations of different pixel operation algorithms on the same ROI sequence vR[.]_m' to respectively provide two vital signs v[t]_q1 and v[t]_q2 as two of the vital signs v[t]_1 to v[t]_M2, or on two ROI sequences vR[.]_m1' and vR[.]_m2' (different two of the ROI sequences vR[.]_1 to vR[.]_M2) to respectively provide two vital signs v[t]_q1 and v[t]_q2. The vital sign extraction block 206 may perform two pixel operations of the same pixel operation algorithm on the different two ROI sequence vR[.]_m3' and vR[.]_m4' to respectively provide two vital signs v[t]_q3 and v[t]_q4.

Figure 8:
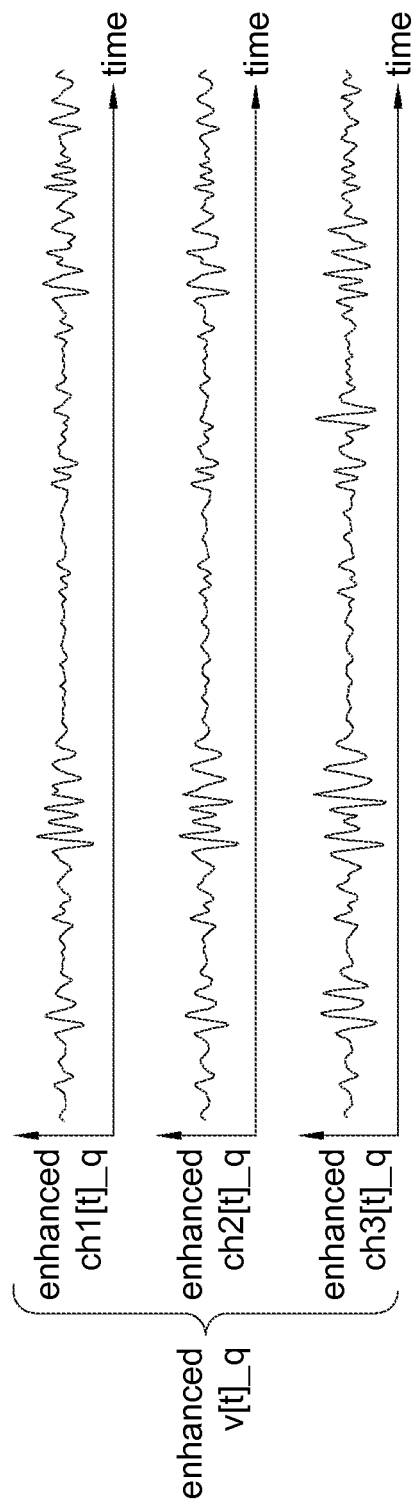

Step 508: optionally, perform signal quality enhancement on one, some or all of the vital signs v[t]_1 to v[t]_Q by the vital sign extraction block 206. For example, to enhance a vital sign v[t]_q indicative of heartbeat pulses, the vital sign extraction block 206 may perform signal quality assessment and outlier removal to suppress noise and remove spikes shown in waveform of the vital sign v[t]_q. The vital sign extraction block 206 may perform band-pass filtering, e.g., by FIR (finite-impulse response) filter, on the vital sign v[t]_q, so as to suppress frequencies exceeding (below and beyond) a proper range of heartbeat rate; e.g., from 40 to 240 bpm (beat per minute). Continuing the illustrative example shown in FIG. 7, FIG. 8 illustrates an exemplary signal enhancement, which is performed on the red, green and blue channel signals ch1[t]_q to ch3[t]_q shown in FIG. 7 to respectively obtain the enhanced channel signals ch1[t]_q to ch3[t]_q in FIG. 8, and the enhanced channel signals ch1[t]_q to ch3[t]_q collectively form the enhanced vital sign v[t]_q.

Similarly, to enhance a vital sign v[t]_q' indicative of respiration movement, the vital sign extraction block 206 may perform band-pass filtering on the vital sign v[t]_q', so as to suppress frequencies exceeding a proper range of respiration rate.

Step 510 (FIG. 5): end the procedure 500 with obtained (enhanced) vital signs v[t]_1 to v[t]_Q.

While respectively performing procedures 300 (FIG. 3) and 500 (FIG. 5), the activity modeling block 204 and the vital sign extraction block 206 (FIG. 2) may cooperate, so an ROI sequence generated by one of the blocks 204 and 206 may be exploited by the other. For example, the activity modeling block 204 may apply step 310 (FIG. 3) to one or some of the ROI sequences vR[.]_to vR[.]_M2 (FIG. 5) provided by the vital sign extraction block 206, and accordingly obtain one or some of the activity signals a[t]_1 to a[t]P. The vital sign extraction block 206 may apply step 506 (and subsequent steps, FIG. 5) to one or some of the ROI sequences aR[.]_1 to aR[.]_M1 (FIG. 3) provided by the activity modeling block 204, and accordingly obtain one or some of the vital signs v[t]_1 to v[t]_Q.

One, some or all of the vital signs v[t]_1 and v[t]_Q may be affected by artifacts caused by movement or motion of the monitored subject. By leveraging activity signal(s) capable of reflecting movement and/or motion of the monitored subject, the filter block 208 may deal with the artifact issue affecting the vital sign(s).

Figure 9:
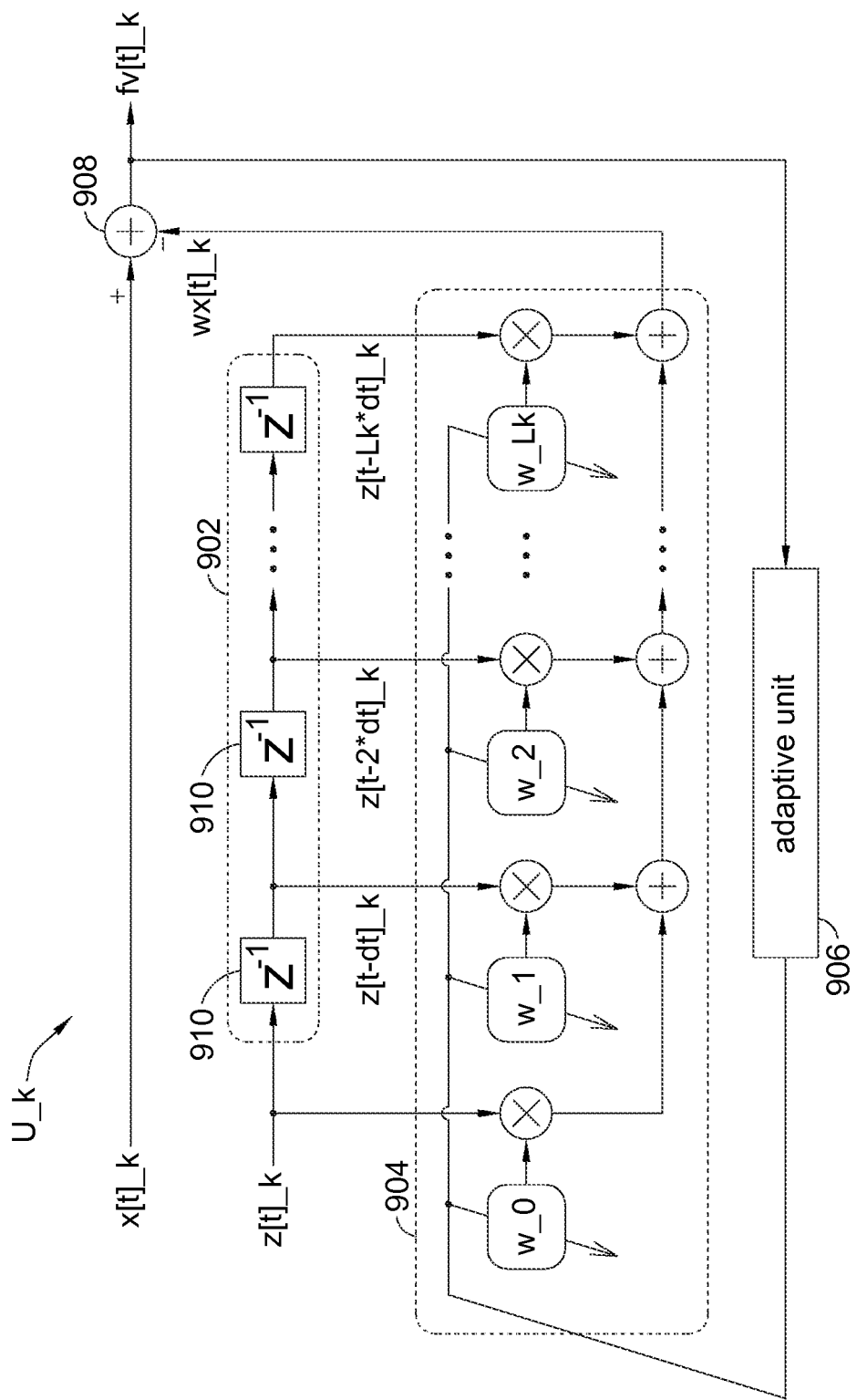
FIG. 9 illustrates an embodiment of a filter unit shown in FIG. 2.

As depicted in FIG. 2, the filter block 208 may include filters U_1 to U_K. Along with FIG. 1 and FIG. 2, please refer to FIG. 9 illustrating an embodiment of a filter U_k (one of the filters U_1 to U_K). The filter U_k is capable of performing filtering on an input signal x[t]_k (e.g., one of the vital signs v[t]_1 to v[t]_Q) in view of a reference signal z[t]_k (e.g., one of the activity signals a[t]_1 to a[t]_P), accordingly suppressing artifact induced by correlation between the reference signal z[t]_k and the input signal x[t]_k, and providing a filtered vital sign rv[t]_k. As shown in FIG. 9, the filter U_k may include a buffer 902, a weighting module 904, an arithmetic node 908 and an adaptive unit 906.

The buffer 902 may include an amount Lk (one or more) of serially coupled delayers 910, each delayer 910 may accept a signal, delay the accepted signal by an interval dt, and provide the delayed result. Collectively with the amount Lk of delayers 910, the buffer 902 is capable of buffering the amount Lk of preceding (delayed) samples x[t-dt]_k, x[t-2*dt]_k to x[t-Lk*dt]_k of the input signal x[t]_k.

The weighting module 904 is capable of weighting the current sample x[t]_k and the amount Lk of preceding samples x[t-dt]_k to x[t-Lk*dt]_k respectively by weighting coefficients w_0 and w_1 to w_Lk, summing the weighted current and preceding samples w0*x[t]_k, w_1*x[t-dt]_k to w_Lk*x[t-Lk*dt]_k, and accordingly providing a current sample of a weighted signal wx[t]_k. The arithmetic node 908 is capable of subtracting the weighted signal wx[t]_k from the input signal x[t] to provide the filtered vital sign fv[t]_k. The adaptive unit 906 is capable of adaptively and dynamically adjusting values of the weighting coefficients w_0 to w_Lk according to the filtered vital sign fv[t]_k.

Function of the filter U_k may be described by analogy and similarity to echo cancellation: the input signal x[t]_k may be analogous to a sound contaminated by echo, and the reference signal z[t]_k may be analogous to echo; subtracting weighted samples of the signal z[t]_k and adaptive feedback control of the weighting coefficients w_0 to w_Lk may be analogous to adaptive echo cancellation, and the resultant filtered vital sign fv[t]_k may be analogous to echo-suppressed sound.

The filter U_k may receive a vital sign v[t]_p (one of the preliminary vital signs v[t]_1 to v[t]_Q) as the input signal x[t]_k, and receive an activity signal a[t]_p (one of the activity signals a[t]_1 to a[t]_P) as the reference signal z[t]_k, so as to filter the vital sign v[t]_p in view of the activity signal a[t]_q; the resultant filtered vital sign fv[t]_k may be regarded as a filtered vital sign fv[t]_k. Two different filters U_k1 and U_k2 of the filters U_1 to U_K may be arranged to respectively filter two vital signs v[t]_q1 and v[t]_q2 of the vital signs v[t]_1 to v[t]_Q in view of the same one activity signal a[t]_p of the activity signals a[t]_1 to a[t]_P, or in view of two activity signals a[t]_p1 and a[t]_p2 of the activity signals a[t]_1 to a[t]_P. Two filters U_k3 and U_k4 of the filters U_1 to U_K may be arranged to respectively filter the same one vital sign v[t]_q of the vital signs v[t]_1 to v[t]_Q in view of two activity signals a[t]_p3 and a[t]_p4 of the activity signals a[t]_1 to a[t]_P.

Figure 10:
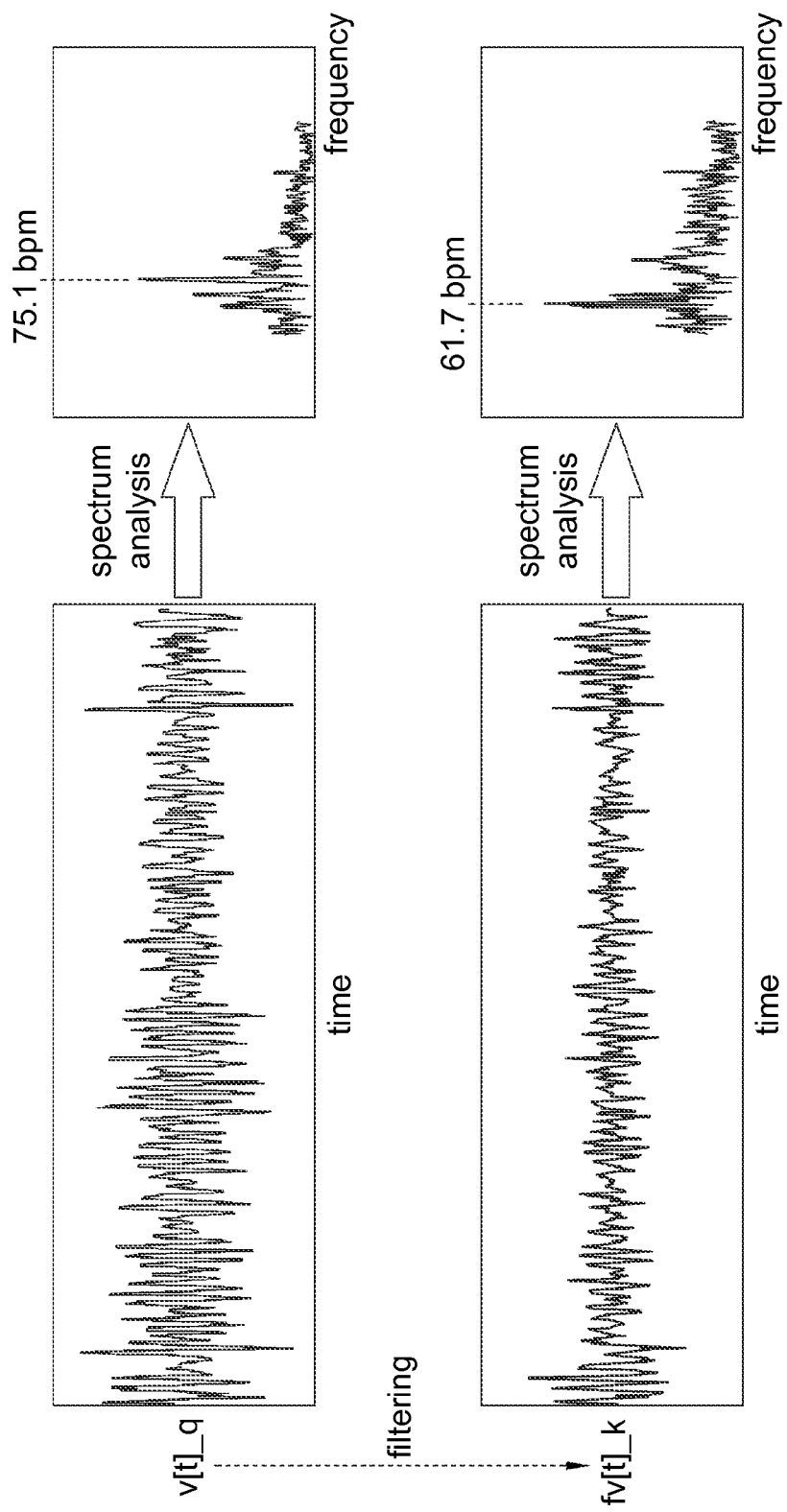
FIG. 10 and FIG. 11 demonstrate illustrative operation examples of the filter shown in FIG. 5.

As an example, FIG. 10 demonstrates a vital sign v[t]_q and an associated filtered vital sign fv[t] which is obtained by filtering the vital sign v[t]_q according to an activity signal a[t]_p (not shown). FIG. 10 also shows spectrums of the two vital signs v[t]_q and fv[t]_q obtained by spectrum analysis, e.g., Fourier transform. The preliminary vital sign v[t]_q, which may be obtained following the example shown in FIG. 6 to FIG. 8, is expected to reflect heartbeat pulses. However, in the example of FIG. 10, the monitored subject is making regular (rhythmical) movements; consequently, the spectrum of vital sign v[t]_q erroneously reflects a peak at 75.1 bpm, instead of a peak at the actual heartbeat rate of the monitored subject. On the other hand, by filtering in view of activity signal, the spectrum of the filtered vital sign fv[t]_q can correctly reflect the actual heartbeat rate of the monitored subject by a peak at 61.7 bpm.

Figure 11:
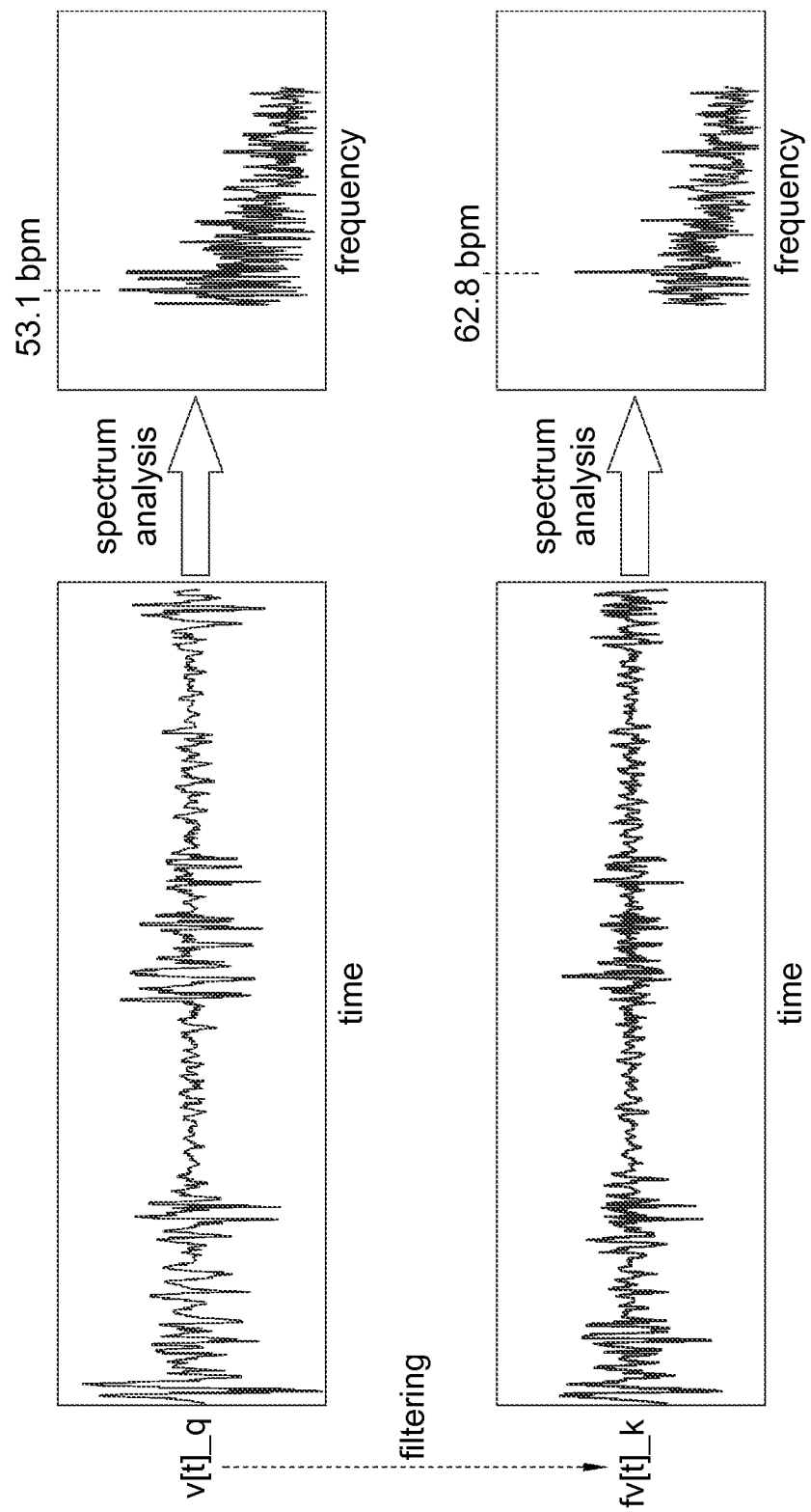

As another example of filtering, FIG. 11 shows another pair of a vital sign v[t]_q and the associated filtered vital sign fv[t], along with their spectrums. The preliminary vital sign v[t]_q in FIG. 11 is also expected to reflect heartbeat pulses. However, in the example of FIG. 11, the monitored subject is making irregular (rhythmless) movements, such as suddenly turning head; consequently, the spectrum of vital sign v[t]_q erroneously reflects a peak at 53.1 bpm, instead of a peak at correct heartbeat rate of the monitored subject. On the other hand, by filtering in view of activity signal, the spectrum of the filtered vital sign fv[t]_q can reflect the actual heartbeat rate of the monitored subject by a peak at 62.8 bpm.

In an embodiment, one or more of the filters U_1 to U_K, such as a filter U_k5, may be arranged to filter an activity signal a[t]_p5 (one of the activity signals a[t]_1 to a[t]_P) in view of another activity signal a[t]p6 (another one of the activity signals a[t]_1 to a[t]_P), or in view of one of the vital signs v[t]_1 to v[t]_Q, or in view of a filtered vital sign fv[t]_k6 provided by another filter U_k6 (k6 different from k5). One or more of the filters U_1 to U_K, such as a filter U_k7, may be arranged to filter a vital sign v[t]_q7 (one of the vital signs v[t]_1 to v[t]_Q) in view of another vital signal v[t]_q8 (another one of the vital signs v[t]_1 to v[t]_Q), or in view of a filtered vital sign fv[t]_k8 provided by another filter U_k8 (k8 different from k7).

Two filters U_k9 and U_k10 of the filters U_1 to U_K may have different amounts of delayers 910 and weighting coefficients, and/or adopt different adaption models to respectively implement their adaptive units 906. Thus, in an embodiment, the filters U_k9 and U_k10 may be arranged to filter the same one of the vital signs v[t]_1 to v[t]_Q in view of the same one of the activity signals a[t]_1 to a[t]P, and accordingly obtain different two filter vital signs fv[t]_k9 and fv[t]_k10.

In an embodiment, for one or more of the filters U_1 to U_K, such as a filter U_k11 which filters an input signal x[t]_k11 in view of a reference signal z[t]_k11 to obtain a filtered vital sign rv[t]_k11, the reference signal z[t]_k11 may be a linear combination of some (or all) of the activity signals a[t]_1 to a[t]_P. Alternatively, the reference signal z[t]_k11 may be a linear combination of: one, some or all of the activity signals a[t]_1 to a[t]_P, along with one, some or all of the vital signs v[t]_1 to v[t]_Q. The linear combination forming the reference signal z[t]_k11 may include one, some or all the filtered vital signs fv[t]_1 to fv[t]_K, except fv[t]_k11.

In an embodiment, for one or more of the filters U_1 to U_K, such as a filter U_k12 which filters an input signal x[t]_k12 in view of a reference signal z[t]_k12 to obtain a filtered vital sign rv[t]_k12, the input signal x[t]_k12 may be a linear combination of some (or all) of the vital signs v[t]_1 to v[t]_Q. Alternatively, the input signal x[t]_k12 may be a linear combination of: one, some or all of the vital signs v[t]_1 to v[t]_Q, along with one, some or all of the activity signals a[t]_1 to a[t]_P. The linear combination forming the input signal x[t]_k12 may include one, some or all the filtered vital signs fv[t]_1 to fv[t]_K, except fv[t]_k12.

Besides the structure shown in FIG. 9, one or more of the filters U1 to U_k, such as a filter U_k', may filter an input signal x[t]_k' in view of multiple reference signals, such as two reference signals za[t]_k' and zb[t]_k' (not shown), and accordingly provide a filtered vital sign fv[t]_k'. For the two reference signals za[t]_k' and zb[t]_k', the filter U_k' may include two buffers 902, two weighting modules 904 and two adaptive units 906. One of the two buffers 902 is capable of buffering an amount La of delayed samples of the signal za[t]_k', and the other one of the buffers 902 is capable of buffering an amount Lb of delayed samples of the signal zb[t]_k'. One of the two weighting modules 904 is capable of weighting delayed (and current) samples of the signal za[t]_k' by weighting coefficients wa_0 to wa_La to provide a sample of a weighted signal wxa[t]_k', the other one of the two weighting modules 904 is capable of weighting delayed (and current) samples of the signal zb[t]_k' by weighting coefficients wb_0 to wb_Lb to provide a sample of a weighted signal wxb[t]_k'. The node 908 is capable of subtracting the signals wxa[t]_k' and wxb[t]_k' from the input signal x[t]_k' to provide the signal fv[t]_k'. One of the adaptive units 906 is capable of adjusting the weighting coefficients wa_0 to wa_La according to feedback of the signal fv[t]_k', and the other one of the adaptive units 906 is capable of adjusting the weighting coefficients wb_0 to wb_Lb according to feedback of the signal fv[t]_k'.

As discussed in FIG. 5, a vital sign v[t]_q (one of the vital signs v[t]1 to v[t]_Q) may include multiple channel signals, such as three channel signals. In an embodiment, three of the filters U_1 to U_K may be grouped as a collective filter, and respectively filter the three channel signals in view of a same reference signal to obtain three filtered vital signs, thus the three filtered vital signs may be included in a collective filtered vital sign to be the output of the collective filter. Alternatively, the multiple channel signals may be linearly combined to form one (or more) combined vital sign, and each combined vital sign may be filtered by one of the filters U_1 to U_K.

Figure 12:
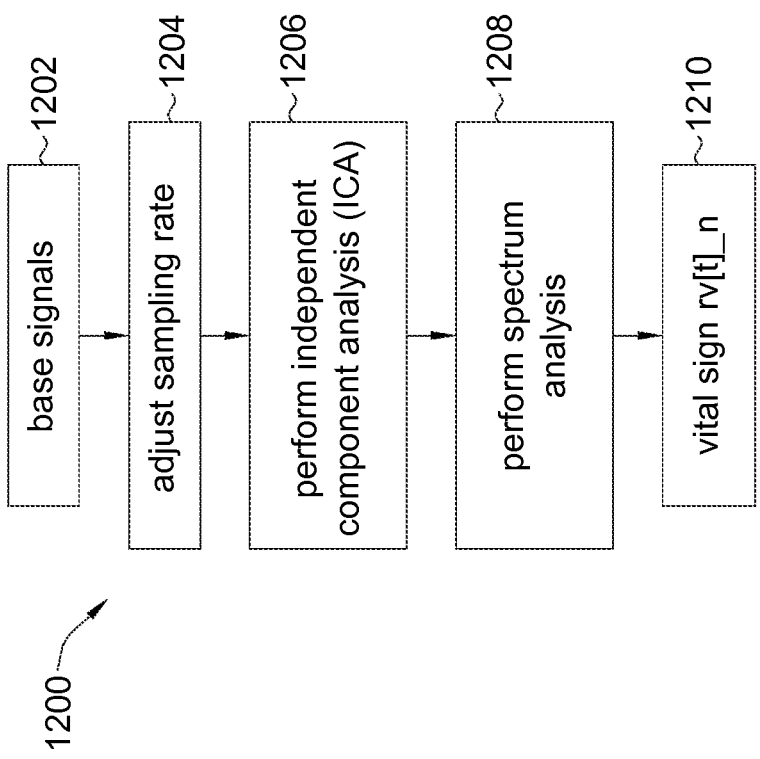
FIG. 12 illustrates a procedure, according to an embodiment of the invention, for vital sign derivation shown in FIG. 1.

Continuing FIG. 1 and FIG. 2, please refer to FIG. 12 illustrating a procedure 1200 according to an embodiment of the invention. The vital sign derivation block 210 (FIG. 2) may execute the procedure 1200 and provide a derived vital sign rv[t]_n as one of the derived vital signs rv[t]_1 to rv[t]_N. Hence, the vital sign derivation block 210 may perform step 110 (FIG. 1) by multiple (concurrent and/or sequential) executions of the procedure 1200 to collectively obtain all the vital signs rv[t]_1 to rv[t]_N of step 110. The procedure 1200 may include the following steps.

Step 1202: to provide the derived signal rv[t]_n, the procedure 1200 may start with multiple base signals. The base signals may be selected from: the vital signs v[t]_1 to v[t]_Q and their channel signals (if any), the filtered vital signs fv[t]_1 to fv[t]_K and their channel signals (if any), the activity signals a[t]_1 to a[t]_P, and, rest of the derived vital signs, i.e., the derived vital signs rv[t]_1 to rv[t]_N excluding rv[t]_n. To obtain one or more of the base signals for the derived vital sign rv[t]_n, the vital sign derivation block 210 may also perform signal pre-processing on signal(s) selected from: the vital signs v[t]_1 to v[t]_Q (and their channel signals), the filtered vital signs fv[t]_1 to fv[t]_K (and their channel signals), the activity signals a[t]_1 to a[t]_P, and the rest derived vital signs, i.e., the derived vital signs rv[t]_1 to rv[t]_N excluding rv[t]_n. For example, the vital sign derivation block 210 may subtract a delayed derived vital sign rv[t-dt']_n' (n' different from n) from the non-delayed derived vital sign rv[t]_n', so the resultant signal (rv[t]_n'-rv[t-dt']_n') may be provided as one of the base signals.

Step 1204: optionally, if the base signals of step 1202 include signals of different sampling rates, then the vital sign derivation block 210 may adjust sampling rates of the signals by up-sampling and/or down-sampling, so as to obtain base signals of a same sampling rate.

Step 1206: perform ICA on the base signals of same sampling rate, and accordingly obtain multiple component signals. Each of the component signals may be time domain signal containing a plurality of temporal (current and/or preceding) samples. By ICA, statistical dependence (e.g., covariance) between every two component signals is minimized. Each of the component signals may also be considered as a vital sign, since the component signals may also reflect vital condition of the monitored subject. For example, one, some or all the component signals may be included in the vital sign v[t]_1 to v[t]_Q to be filtered in view of the activity signal(s). Alternatively, one, some or all the component signals may be included in the derived vital signs rv[t]_1 to rv[t]_N excluding rv[t]_n.

Step 1208: by the vital sign derivation block 210, perform spectrum analysis, e.g., Fourier transform, Fast Fourier transform, windowed Fourier transform, discrete cosine transform, wavelet transform, etc., on the component signal(s) to obtain associated spectrum(s), and identify a characteristic value of the spectrum(s) to provide a sample of the derived vital sign rv[t]_n.

In an embodiment, the vital sign derivation block 210 may first select one of the time domain component signals (e.g., by comparing power of the component signals and selecting the one with greatest power), then perform the spectrum analysis on the selected component signal (e.g., over samples at times t, (t-dt), (t-2*dt), . . . , (t-J4*dt)) to transform it to a frequency domain, and hence identify a characteristic value of the spectrum (e.g., a frequency with maximum spectrum magnitude) as a sample of the derived vital sign rv[t]_n.

Alternatively, the vital sign derivation block 210 may perform spectrum analysis on each of the component signals over samples at times t, (t-dt), (t-2*dt), . . . , (t-J4*dt), and accordingly obtain multiple spectrums, and hence identify a characteristic value of the spectrums (e.g., a frequency with maximum spectrum magnitude over all the spectrums) as a sample of the derived vital sign rv[t]_n.

Step 1210: end the procedure 1200 with obtained derived vital sign rv[t]_n.

Figure 13:
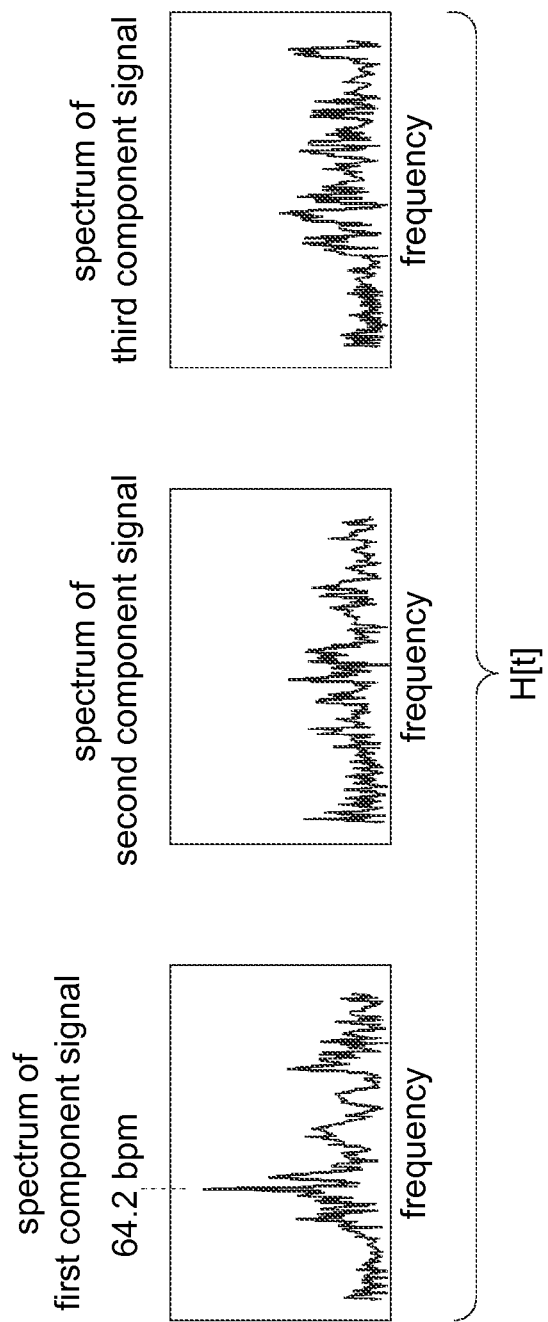
FIG. 13 and FIG. 14 demonstrate illustrative operation examples of the procedure shown in FIG. 12.

Together with steps 106, (108) and 110 (FIG. 1), a derived vital sign H[t] (one of the derived vital signs rv[t]_1 to rv[t]_N) indicative of temporal heartbeat rate may be provided by: identifying head tracking ROIs (e.g., ROIs in FIG. 6) and obtaining three channel signals ch1[$t$]_q1, ch2[$t$]_q1 and ch3[$t$]_q1 (e.g., the channel signals shown in FIG. 8) during procedure 500 (FIG. 5) of step 106, and selecting the three channel signals ch1[$t$]_q1, ch2[$t$]_q1 (or three filtered vital signs obtained by applying activity filtering to the three channel signals ch1[$t$]_q1, ch2[$t$]_q1 and ch3[$t$]_q1 in view of an activity signal, step 108) as base signals in step 1202 (FIG. 12). Continuing the example in FIG. 8, FIG. 13 is an illustrative example showing spectrums obtained by applying spectrum analysis (step 1208, FIG. 12) to three component signals which are obtained by performing ICA (step 1206) on three channel signals, e.g., the three channel signals ch1[$t$]_q1, ch2[$t$]_q1 and ch3[$t$]_q1 in FIG. 8. In the example of FIG. 13, the spectrum of the first component signal has a magnitude peak, at frequency 64.2 bpm, maximizing over the three component signals, thus the frequency 64.2 bpm may be provided as a current sample of the derived vital sign H[t] (step 1210), so as to indicate that the current heartbeat rate (evaluated over an elapsed interval including times t, (t-dt), (t-2*dt), . . . , (t-J4*dt)) is 64.2 bpm.

Besides the derived vital sign H[t] indicative of heartbeat rate, a derived vital sign R[t] (one of the derived vital signs rv[t]_1 to rv[t]_N excluding H[t]s) indicative of temporal respiration rate may be provided following the procedure 1200. To form the derived vital sign R[t], the base signals (step 1202) may including two vital signs v[t]_r1 and v[t]_r2 (two of the vital signs v[t]_1 to v[t]_Q and fv[t]_1 to fv[t]_K), along with the aforementioned derived vital sign H[t] provided by other execution of the procedure 1200.

According to the procedure 500 (FIG. 5), forming the vital sign v[t]_r1 may include: in step 504, identifying an ROI sequence vR[.]_r1 (one of the ROI sequences vR[.]_1 to vR[.]_M2) for tracking head and/or chest (neck); and, in step 506, obtaining a current sample of the vital sign v[t]_r1 (one of the vital signs v[t]_1 to v[t]_Q) by applying a first pixel operation to a current ROI vR[t]_r1; optionally, the vital sign v[t]_r1 may also be filtered by activity signal(s) in step 108 (FIG. 1). Forming the vital sign v[t]_r2 may include: in step 506, obtaining a current sample of the vital sign v[t]_r2 by applying a second pixel operation which works on a difference between a current ROI vR[t]_r1 and a preceding ROI vR[t-dt]_r1 of the ROI sequence vR[.]_r1; optionally, the vital sign v[t]_r2 may also be filtered by activity signal(s) in step 108 (FIG. 1).

With the vital signs v[t]_r1, v[t]_r2 and the derived vital sign H[t], the vital sign R[t] may be obtained by: in step 1202, further applying signal pre-processing to the derived vital sign H[t] to obtain a current sample of a pre-processed derived vital sign (e.g., a beat-by-beat heart rate) BB[t] by (H[t]-H[t-dt']); in step 1208, applying ICA to the vital sign v[t]_r1, v[t]_r2 and the pre-processed derived vital sign BB[t] to obtain multiple (e.g., three) component signals, selecting one of the component signals (e.g., by comparing power or spectrums of the component signals), and then applying spectrum analysis to the selected component signal to find a characteristic value (e.g., the frequency where maximum spectrum magnitude occurs) as a current sample of the derived vital sign R[t], which is capable of indicating respiration rate of the monitored subject. The pre-processed derived vital sign BB[t], e.g., a beat-by-beat heart rate, is leveraged to generate the derived vital sign R[t] because heartbeat rate speeds up during breathing-in, and slows down during breathing-out; therefore, the vital sign BB[t] is indicative of breathing movement.

Figure 14:
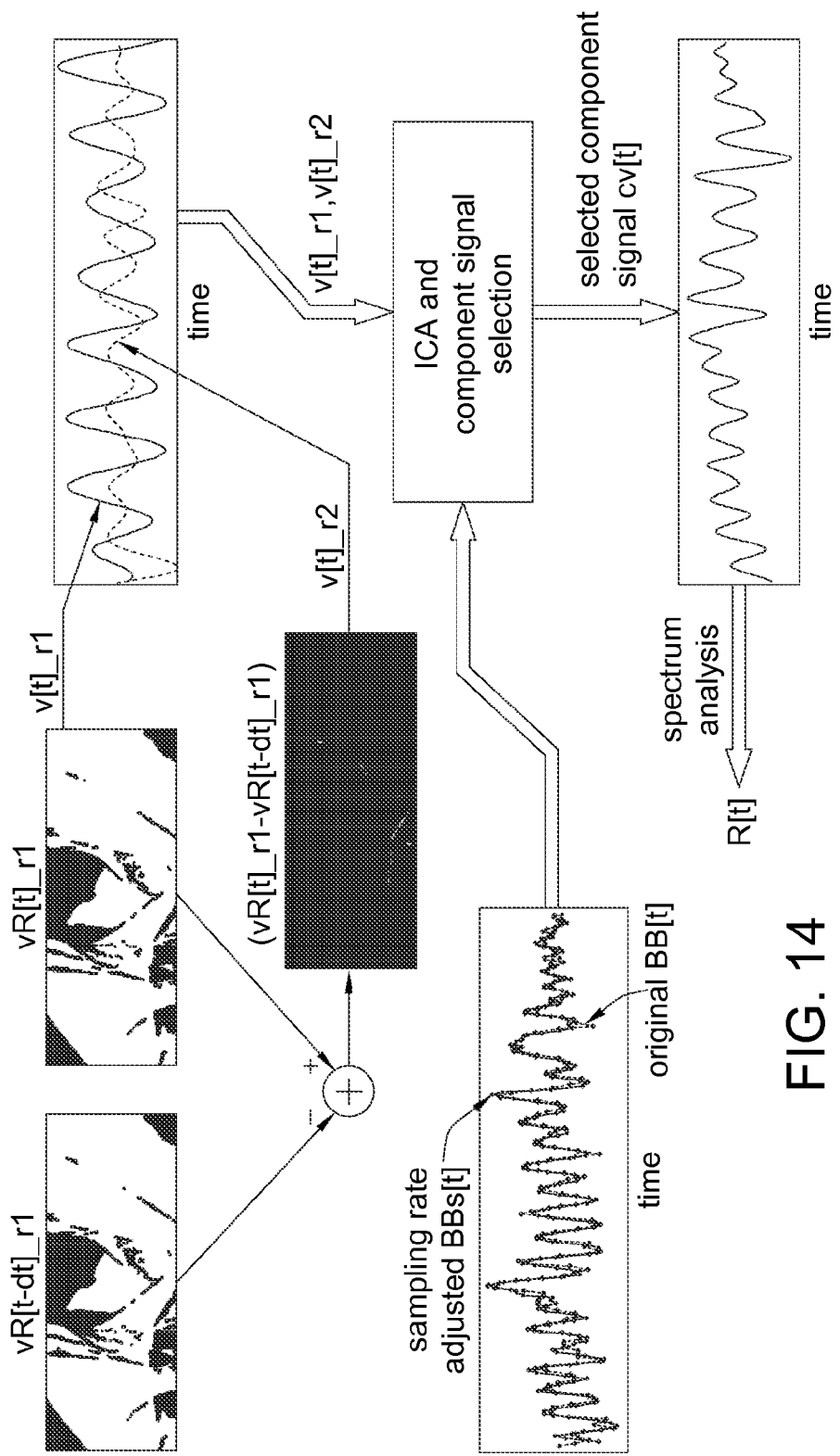

As an illustrative example, FIG. 14 demonstrates operations involved in forming the vital signs v[t]_r1 and v[t]_r2, and resultant waveforms of the vital signs v[t]_r1 and v[t]_r2. In the example of FIG. 14, the original pre-processed derived vital sign BB[t] has a sampling rate different from the sampling rate of the vital signs v[t]_r1 and v[t]_r2, thus sampling rate of the original derived vital BB[t] is adjusted (e.g., by up-sampling or interpolation), also in step 1202 (FIG. 12), to obtain an adjusted derived vital sign BBs[t], which has a sampling rate identical to that of the vital signs v[t]_r1 and v[t]_r2. Applying ICA to the vital signs v[t]_r1, v[t]_r2 and BBs[t] may obtain three component signals (not shown); and, by proper selection, one of the component signal, e.g., the component signal cv[t], may correctly reflect breathing movement by its waveform. Thus, by performing spectrum analysis on the component signal cv[t], a current sample of the derived vital sign R[t], indicative of respiration rate, may be obtained.

In the procedure 1200, step 1204 may be optional, and step 1206 may also be optional. In an embodiment, the vital sign derivation block 210 may select a single base signal in step 1202, and then perform spectrum analysis to the base signal in step 1208 to obtain a derived vital sign; i.e., step 1206 may be omitted in such embodiment. For example, the vital sign derivation block 210 may utilize the filtered vital sign fv[t]_k shown in FIG. 11 as a base signal, and apply spectrum analysis to it, so the frequency 62.8 bpm may be provided as a sample of a derived vital sign.

In addition to the vital signs v[t]_1 to v[t]_Q, the filter block 208 (FIG. 2) may also perform filtering of step 108 (FIG. 1) to one, some or all of the derived vital signs rv[t]_1 to rv[t]_N, and accordingly obtain a subset of the filtered vital signs fv[t]_1 to fv[t]_K.

Figure 15:
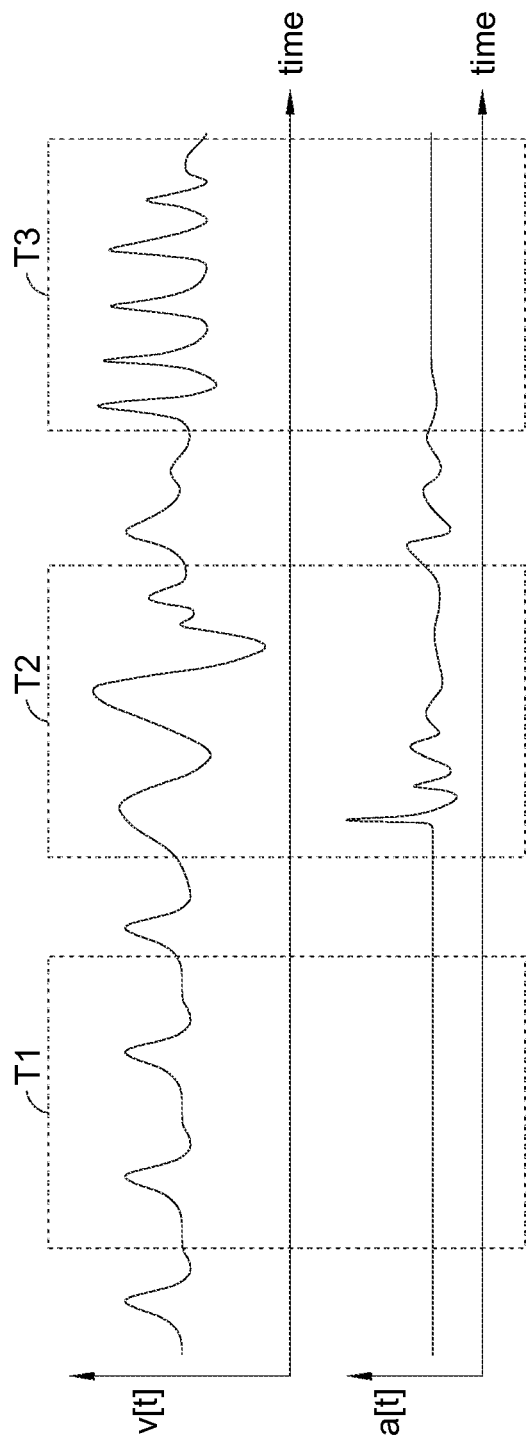
FIG. 15 illustrates a principle for joint decision shown in FIG. 1.

Along with FIG. 1 and FIG. 2, please refer to FIG. 15 illustrating temporal waveforms of a vital sign v[t] (e.g., one of the vital signs v[t]_1 to v[t]_Q, fv[t]_1 to fv[t]_K and rv[t]_1 to rv[t]_N) and an activity signal a[t] (one of the activity signal a[t]_1 to a[t]_P) to exemplarily explain operation principle for joint decision of step 112 (FIG. 1) and the joint decision maker 212 (FIG. 2). For example, the vital sign v[t] may reflect heartbeat pulse or breathing motion of a monitored subject, and the activity signal a[t] may reflect activity of the monitored subject. In an episode T1, the monitored subject is healthily sleeping or at rest, so the vital sign v[t] shows regularly periodic pulses, and the activity signal a[t] reflects minor activity with nearly flat line. In an episode T2, the monitored subject is healthily moving or exercising, so the vital sign v[t] shows irregular waves, and the activity signal a[t] also fluctuates. In an episode T3, the monitored subject is in abnormal condition, the vital sign v[t] shows irregular waves, and the activity signal a[t] reflects no activity. By the vital sign v[t] alone (without leveraging the activity signal a[t]), it is difficult to distinguish the episodes T2 and T3, since the vital sign v[t] becomes irregular in both the episodes. On the other hand, by the activity signal a[t] alone (without leveraging the vital sign v[t]), it is also difficult to discriminate the episodes T1 and T3, since the activity signal a[t] maintains flat in both the episodes. It is therefore understood that both the activity signal a[t] and the vital sign v[t] should be jointly considered to correctly determine health condition of the monitored subject.

Figure 16:
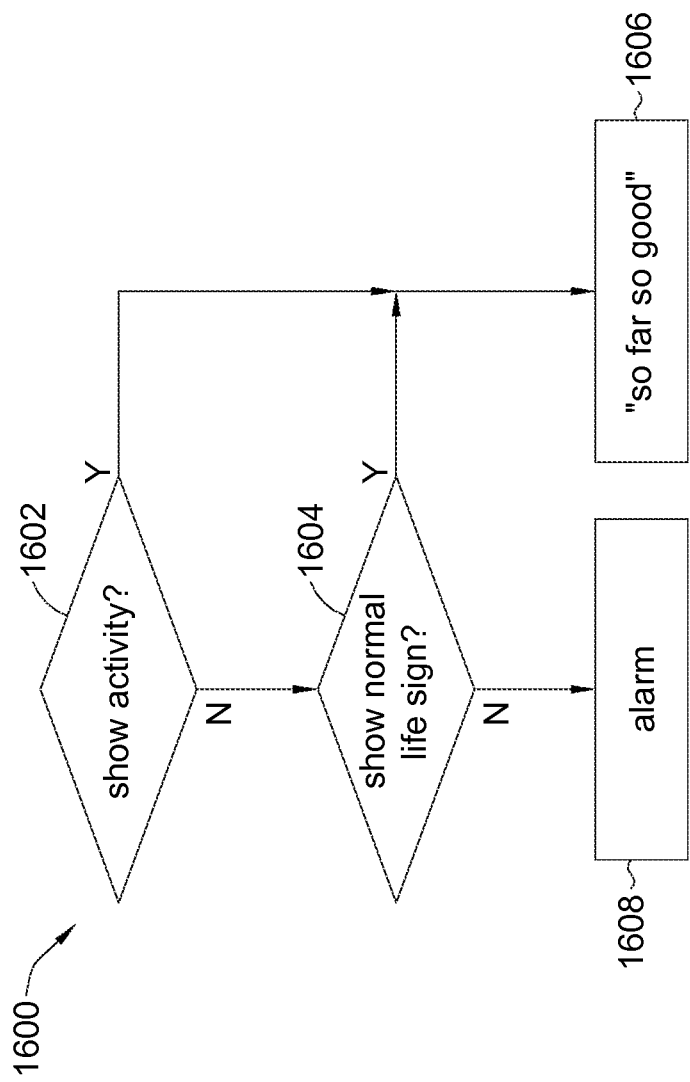
FIG. 16 illustrates a procedure, according to an embodiment of the invention, for making joint decision shown in FIG. 1.

Continuing FIG. 1 and FIG. 2, please refer to FIG. 16 illustrating a procedure 1600 according to an embodiment of the invention; the joint decision maker 212 (FIG. 2) may implement step 112 according to the procedure 1600. The procedure 1600 may include the following steps.

Step 1602: by the joint decision maker 212, determine whether the monitored subject shows activity according to whether each of one, some or all of the activity signals a[t]_1 to a[t]_P exceeds a predetermined activity threshold range (e.g., a lower bound). If true, proceed to step 1606, otherwise proceed to step 1604. For example, the joint decision maker 212 may exploit an activity signal a[t]_s1 (one of the activity signals a[t]_1 to a[t]_P) as an activity indicator for detecting occurrence of activity. If a current sample, or a statistical value (e.g., mean, maximum, or minimum, etc.) calculated over samples of an elapsed duration from time (t-J5*dt) to current time t, of the activity signal a[t]_s1 is greater than a lower bound LB_s1 (as an activity threshold range associated with the activity signal a[t]_s1), the joint decision maker 212 may determine that the monitored subject shows normal activity at current time t.

Alternatively, the joint decision maker 212 may exploit multiple activity signals (some or all of the activity signals a[t]_1 to a[t]_P), such as two activity signals a[t]_s1 and a[t]_s2, as activity indicators. With multiple activity indicators, there are various algorithms to determine if there is activity. For example, the joint decision maker 212 may determine existence of activity according to: If a current sample (or a statistic value calculated over an elapsed duration) of the activity signal a[t]_s1 exceeds an activity threshold range R_s1 (e.g., a first lower bound LB_s1). If a current sample (or a statistic value calculated over an elapsed duration) of the activity signal a[t]_s2 exceeds an activity threshold range R_s2 (e.g., a second lower bound LB_s2). The joint decision maker 212 may confirm existence of activity if both the activity threshold ranges R_s1 and R_s2 are exceeded. Alternatively, the joint decision maker 212 may confirm existence of activity if either one of the activity threshold ranges R_s1 and R_s2 is exceeded.

Alternatively, leveraging multiple activity indicators such as the two activity signals a[t]_s1 and a[t]_s2, the joint decision maker 212 may first linearly combine the two activity signals a[t]_s1 and a[t]_s2, then determine if activity exists by comparing whether the resultant linear combination exceeds a predetermined activity threshold range.

Step 1604: by the joint decision maker 212, determine whether the monitored subject show normal life sign according to whether each of one, some or all of the vital signs v[t]_1 to v[t]_Q, the filtered vital signs fv[t]_1 to fv[t]_K and the derived vital signs rv[t]_1 to rv[t]_N does not exceed an associated predetermined vital threshold range. If true, proceed to step 1606, otherwise proceed to step 1608. Each vital threshold range may include a single lower bound, a single upper bound, or both the lower bounds and the upper bounds.

For example, the joint decision maker 212 may exploit a single vital sign xv[t]_s3 (one of the vital signs v[t]_1 to v[t]_P, fv[t]_1 to fv[t]_K and rv[t]_1 to rv[t]_N) as a vital indicator for detecting presence of normal life sign. If a current sample, or a statistical value (e.g., mean, maximum, or minimum, etc.) calculated over samples of an elapsed duration from time (t-J6*dt) to current time t, of the vital sign xv[t]_s3 is greater than a lower bound LB_s3 of a vital threshold range R_s3 associated with the vital sign xv[t]_s3, and is less than a upper bound UB_s3 (if exists) of the vital threshold range R_s3, the joint decision maker 212 may determine that the monitored subject shows normal life sign at current time t. Otherwise, if the vital sign xv[t]_s3 is less than the lower bound LB_s3 or greater than the upper bound UB_s3 (if exists), the joint decision maker 212 may determine that the monitored subject does not show normal life sign at current time t.

Alternatively, the joint decision maker 212 may exploit multiple vital signs (some or all of the vital signs v[t]_1 to v[t]_P, fv[t]_1 to fv[t]_K and rv[t]_1 to rv[t]_N), like two vital signs v[t]_s3 and v[t]_s4, as vital indicators. With multiple vital indicators, there are various algorithms to determine presence of normal life sign. For example, the joint decision maker 212 may determine presence of normal life sign: if a current sample (or a statistic value calculated over an elapsed duration) of the vital sign xv[t]_s3 falls in an associated vital threshold range R_s3, and, if a current sample (or a statistic value calculated over an elapsed duration) of the vital sign xv[t]_s4 falls in an associated vital threshold range R_s4. The joint decision maker 212 may confirm presence of normal life sign if both the vital threshold ranges R_s3 and R_s4 are not exceeded. Alternatively, the joint decision maker 212 may confirm existence of activity if either one of the activity threshold ranges R_s1 and R_s2 is not exceeded.

Alternatively, the joint decision maker 212 may first linearly combine multiple vital indicators, and then determine if there shows normal life sign by comparing whether the resultant linear combination falls in a predetermined vital threshold range.

Step 1606: by the joint decision maker 212, summarize current health condition of the monitored subject by categorizing result of life sign monitoring to a normal episodes reflecting "so far so good." Then the procedure 1600 may iterate back to step 102 (FIG. 1) to continue life sign monitoring.

Step 1608: by the joint decision maker 212, categorize current result of life sign monitoring to an abnormal episode, which may lead to an alarm for immediate medical attention of the monitored subject.

The processor 200 (FIG. 2) may output associated report signal for reporting episode provided according to the procedure 1600, hence the episode may be presented to user(s) (e.g., medical personnel) of the processor 200 by visual display (e.g., green light and red light respectively for the normal and abnormal episodes, and/or showing icons, texts, animations via screen) and/or by audio sound.

Figure 17:
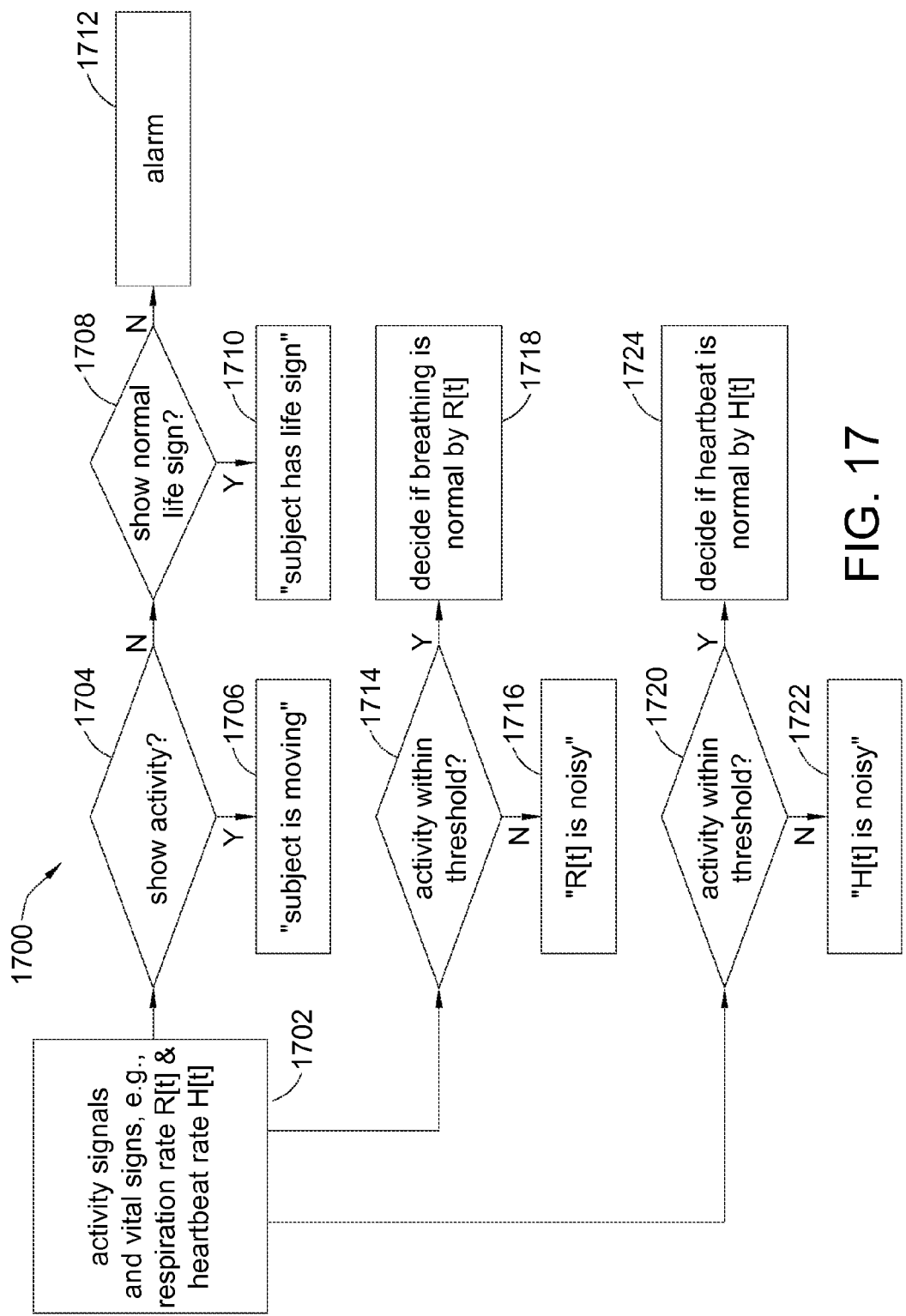
FIG. 17 illustrates a procedure, according to an embodiment of the invention, for making joint decision shown in FIG. 1.

Along with FIG. 1 and FIG. 2, please refer to FIG. 17 illustrating a procedure 1700 according to an embodiment of the invention; beside the procedure 1600, the joint decision maker 212 (FIG. 2) may also implement step 112 by the procedure 1700. The procedure 1700 may include the following steps.

Step 1702: start the procedure 1700 with one or more activity indicators selected from the activity a[t]_1 and a[t]_P, as well as one more vital indicators selected from the vital signs v[t]_1 to v[t]_P, fv[t]_1 to fv[t]_K and rv[t]_1 to rv[t]_N. In FIG. 17, the derived vital sign H[t] indicative of heartbeat rate (discussed in FIG. 13), and the derived vital sign R[t] indicative of respiration rate (discussed in FIG. 14), are utilized as two vital indicators.

Step 1704: according to whether each activity indicator is beyond (exceeds) an activity threshold range (e.g., a lower bound), the joint decision maker 212 (FIG. 2) determines if there is activity. If true, the joint decision maker 212 may proceed to step 1706. If false, the joint decision maker 212 may proceed to step 1708. Similar to step 1602 (FIG. 16), the joint decision maker 212 may adopt an activity indicator, and decide existence of activity according to if the activity indicator is greater than a lower bound of the associated activity threshold range. Alternatively, the joint decision maker 212 may leverage multiple activity indicators, and decide existence of activity according to: whether all the activity indicators are greater than respective lower bounds of their associated activity threshold ranges; or, whether any of the multiple activity indicators is greater than a lower bound of its associated activity threshold range; or, whether combination of the activity indicators is greater than a lower bound of an associated activity threshold range.

Step 1706: by the joint decision maker 212, direct to an episode reflecting "subject is moving." Then the procedure 1700 may iterate back to step 102 (FIG. 2) for continuing monitoring.

Step 1708: similar to step 1604 (FIG. 16), determine if normal life sign presents according to whether each vital indicator is within an associated vital threshold range. If true, proceed to step 1710. If false, proceed to step 1712. The joint decision maker 212 may only consult a single vital indicator, and decide presence of life sign according to if the vital indicator is between a lower bound and an upper bound of the associated vital threshold range. Alternatively, the joint decision maker 212 may leverage multiple vital indicators, and decide presence of life sign according to: whether all the vital indicators are within their associated vital threshold ranges; or, whether any of the multiple vital indicators is within the associated vital threshold range; or, whether combination of the vital indicators falls in an associated vital threshold range. The vital threshold ranges associated with different vital indicators may be identical or different; e.g., lower bounds and/or upper bounds of two vital threshold ranges may be of different values.

Step 1710: categorize life sign to an episode reflecting "subject has life sign." Then the procedure 1700 may iterate back to step 102 (FIG. 1) to keep on monitoring.

Step 1712: by the joint decision maker 212, categorize result of life sign monitoring to an abnormal episode, which may lead to an alarm for immediate medical attention of the monitored subject.

Step 1714: continuing step 1702, the joint decision maker 212 may determining if activity of the monitored subject is within a threshold according to whether each activity indicator is within a respiration rate reliability range (e.g., below a lower bound of the associated respiration rate reliability range). If true, the joint decision maker 212 may proceed to step 1718. If false, the joint decision maker 212 may proceed to step 1716.

Step 1716: direct to an episode reflecting "R[t] is noisy," i.e., a current respiration rate reading provided by the derived vital sign R[t] may be interfered by activity.

Step 1718: decide if breathing is normal according to whether the derived vital sign R[t] is within the respiration rate range. From step 1714 to step 1718, the joint decision maker 212 may conclude that the current respiration rate reading provided by the derived vital sign R[t] is reliable, since interference owing to activity is low. Hence, the joint decision maker 212 may rely on the derived vital sign R[t] to correctly determine if breathing of the monitored subject is normal. If breathing is normal, the procedure 1700 may reflect an episode for "breathing is normal" (not shown), and iterate to step 102 (FIG. 1); otherwise, the joint decision maker 212 may direct to an alarm episode (not shown).

Step 1720: continuing step 1702, the joint decision maker 212 may determine if activity of the monitored subject is within a threshold according to whether each activity indicator is within a heartbeat rate reliability range (e.g., below a lower bound of the associated heartbeat rate reliability range). If true, the joint decision maker 212 may proceed to step 1724. If false, the joint decision maker 212 may proceed to step 1722.

Step 1722: direct to an episode reflecting "H[t] is noisy," i.e., a current heartbeat rate reading provided by the derived vital sign H[t] may be interfered by activity.

Step 1724: decide if heartbeat is normal according to whether the derived vital sign R[t] is within the heartbeat rate range. From step 1720 to step 1724, the joint decision maker 212 may conclude that the current heartbeat rate reading provided by the derived vital sign H[t] is reliable, since interference owing to activity is low. Hence, the joint decision maker 212 may rely on the derived vital sign H[t] to further determine if heartbeat of the monitored subject is normal. If heartbeat is normal, the procedure 1700 may reflect an episode for "heartbeat is normal" (not shown), and iterate to step 102 (FIG. 1); otherwise, the joint decision maker 212 may direct to an alarm episode (not shown).

According to steps 1714, 1716 and 1718 or 1720, 1722 and 1724, it is understood that, by utilizing activity signal(s), the joint decision maker 212 may interpret vital sign(s) to determine whether each vital sign is reliable or noisy (interfered due to activity). By branching form steps 1714 to 1716 (or 1720 to 1722), false alarm can be effectively avoided. In steps 1704, 1714 and 1720, the joint decision maker 212 may respectively select identical or different subsets of the activity signals a[t]_1 to a[t]_P as the activity indicators. For detecting exceeding activity, the respiration rate reliability range in step 1716 and the heartbeat rate reliability range in step 1720 may be different or identical.

To sum up, the invention provides automatic, remote, noninvasive and effective life sign monitoring exploiting video signal, which may be handily captured by low-cost, non-contact, easily deployed video camera, to obtain both activity signal(s) and vital sign(s), and then collectively leveraging information of different aspects respectively provided by the activity signal(s) and vital sign(s). For example, the vital sign(s) may be filtered in view of the activity signal(s), so as to improve signal quality (e.g., signal to noise ratio) and accuracy of the vital sign(s); and/or, by jointly considering the vital sign(s) and the activity signal(s), life sign condition of the monitored subject may be correctly categorized to simplified episodes, in addition to detailed numerical readings, for convenience, efficiency and fast responding of medical personnel.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A life sign monitoring controller, comprising:
   an interface circuit for obtaining a video signal;
   an activity modeling circuit for performing an activity modeling on the video signal to provide an activity signal;
   a vital sign extraction circuit for performing a vital sign extraction on the video signal to provide a vital sign; and
   a filter circuit for performing a filtering on the vital sign in view of the activity signal to suppress a correlation between the activity signal and the vital sign, and accordingly providing a filtered vital sign.

2. The controller of claim 1 further comprising:
   a joint decision maker for providing a joint decision for categorizing result of life sign monitoring to one of a plurality of predetermined episodes, according to the filtered vital sign and whether the activity signal exceeds an activity threshold range.

3. The controller of claim 1, wherein the filter block comprises:
   a buffer for buffering an amount of preceding samples of the activity signal;
   a weighting module for weighting the amount of preceding samples respectively by a same amount of weighting coefficients, summing the amount of weighted preceding samples, and accordingly providing a current sample of a weighted signal; and
   an arithmetic node for subtracting the weighted signal from the vital sign to provide the filtered vital sign.

4. The controller of claim 3 further comprising:
   an adaptive unit for adjusting the weighting coefficients according to the filtered vital sign.

5. The controller of claim 1, wherein the vital sign extraction block performs the vital sign extraction by identifying an ROI from each of a plurality of frames of the video signal; and performing a pixel operation on pixels of a number of ROIs to provide a sample of the vital sign.

6. The controller of claim 1, wherein the filtered vital sign comprises a plurality of channel signals, and the controller further comprising:
   a vital sign derivation block for:
   performing an ICA on the channel signals, and accordingly providing a plurality of component signals; and
   providing a derived vital sign according to the component signals.

7. The controller of claim 6, wherein the vital sign derivation block is further for:
   performing spectrum analysis on the component signals to obtain spectrums; and
   identifying a characteristic value of the spectrums to provide a sample of the derived vital sign.

8. The controller of claim 1 further comprising:
   a vital sign derivation block for:
   providing a first derived vital sign and performing a signal pre-processing on the first derived vital sign;
   performing an ICA on the pre-processed first derived vital sign and the vital sign to provide a plurality of component signals;
   providing a second derived vital sign according to the component signals.

9. The controller of claim 1, wherein the activity modeling block performs the activity modeling by identifying an ROI from each of a plurality of frames of the video signal; and performing an ROI operation on a number of ROIs to provide the activity signal.

* * * * *